US010398921B1

(12) United States Patent
Walsh et al.

(10) Patent No.: US 10,398,921 B1
(45) Date of Patent: Sep. 3, 2019

(54) METHODS OF ADJUSTING STIFFNESS AND FLEXIBILITY IN DEVICES, APPARATUS AND EQUIPMENT

(71) Applicant: Alliance Design and Development Group, Inc., Matawan, NJ (US)

(72) Inventors: Robert Walsh, Matawan, NJ (US); Peter B. Tarlton, Pangbourne (GB)

(73) Assignee: Alliance Design and Development Group, Inc., Matawan, NJ (US)

( * ) Notice: Subject to any disclaimer, the term of this patent is extended or adjusted under 35 U.S.C. 154(b) by 23 days.

(21) Appl. No.: 15/655,588

(22) Filed: Jul. 20, 2017

Related U.S. Application Data

(63) Continuation-in-part of application No. 14/961,874, filed on Dec. 7, 2015, now Pat. No. 9,737,747, which
(Continued)

(51) Int. Cl.
*A63B 53/16* (2006.01)
*A63B 21/00* (2006.01)
(Continued)

(52) U.S. Cl.
CPC ........ *A63B 21/00185* (2013.01); *A01K 87/00* (2013.01); *A01L 7/06* (2013.01);
(Continued)

(58) Field of Classification Search
CPC .............. A63B 21/00185; A63B 59/20; A63B 21/4037; A63B 21/4029; A63B 2102/18;
(Continued)

(56) References Cited

U.S. PATENT DOCUMENTS 3,461,593 A * 8/1969 Martuch ................ A01K 87/00
43/18.5
3,638,941 A 2/1972 Kulkens
(Continued)

OTHER PUBLICATIONS

Hopley, M., "Guide to Adjustable Golf Clubs," May 28, 2014, http://www.golfalot.com/equipment-news/guide-to-adjustable-golf-clubs-2876.aspx.
(Continued)

*Primary Examiner* — Stephen L Blau
(74) *Attorney, Agent, or Firm* — Law Office of Carl Giordano, PC

(57) ABSTRACT

A resilient rod that provides adjustable directional resistance is disclosed. In one aspect of the invention, a resistance level may be determined based on a thickness of the rod and a position of an applied force with respect to a fulcrum point. In another aspect of the invention, at least one spine may be attached to the beam to increase a diameter of the beam along one axis. A resistance level may be determined based on a thickness of the rod, a position of an applied force and an orientation of the at least one spine with regard to the direction of the applied force. In other aspects of the invention, the resilient rods may be incorporated into various equipment that provide for adjustable resistance levels. In still other aspects of the invention, the resilient rod may be incorporated into medical devices that provide adjustable support for injured limbs or joints.

17 Claims, 27 Drawing Sheets

Related U.S. Application Data is a continuation of application No. 13/622,331, filed on Sep. 18, 2012, now abandoned.

(60) Provisional application No. 61/585,315, filed on Jan. 11, 2012.

(51) Int. Cl.

| | | |
|---|---|---|
| *A01K 87/00* | (2006.01) | |
| *A01L 7/06* | (2006.01) | |
| *A63C 5/07* | (2006.01) | |
| *A63B 59/70* | (2015.01) | |
| *A63B 53/10* | (2015.01) | |
| *A63B 49/02* | (2015.01) | |
| *A63B 23/12* | (2006.01) | |
| *A63B 23/035* | (2006.01) | |
| *A63B 21/04* | (2006.01) | |
| *A63B 21/02* | (2006.01) | |
| *A61F 5/01* | (2006.01) | |
| *A63B 59/50* | (2015.01) | |
| *A63B 102/18* | (2015.01) | |
| *A63B 59/20* | (2015.01) | |
| *A63B 102/24* | (2015.01) | |
| *A63B 71/06* | (2006.01) | |
| *A63B 71/02* | (2006.01) | |
| *A63B 24/00* | (2006.01) | |
| *A63B 22/06* | (2006.01) | |
| *A63B 22/02* | (2006.01) | |
| *A63B 22/00* | (2006.01) | |
| *A63B 5/06* | (2006.01) | |
| *B33Y 80/00* | (2015.01) | |

(52) U.S. Cl.
CPC ...... *A61F 5/0123* (2013.01); *A63B 21/00069* (2013.01); *A63B 21/00072* (2013.01); *A63B 21/026* (2013.01); *A63B 21/0442* (2013.01); *A63B 21/4023* (2015.10); *A63B 23/03541* (2013.01); *A63B 23/1209* (2013.01); *A63B 49/02* (2013.01); *A63B 53/10* (2013.01); *A63B 59/70* (2015.10); *A63C 5/07* (2013.01); *A63B 5/06* (2013.01); *A63B 21/0004* (2013.01); *A63B 21/4029* (2015.10); *A63B 21/4037* (2015.10); *A63B 22/0056* (2013.01); *A63B 22/02* (2013.01); *A63B 22/0605* (2013.01); *A63B 22/0664* (2013.01); *A63B 24/0062* (2013.01); *A63B 59/20* (2015.10); *A63B 59/50* (2015.10); *A63B 71/0622* (2013.01); *A63B 2071/027* (2013.01); *A63B 2071/0694* (2013.01); *A63B 2102/18* (2015.10); *A63B 2102/24* (2015.10); *A63B 2209/02* (2013.01); *A63B 2210/50* (2013.01); *A63B 2220/24* (2013.01); *A63B 2220/40* (2013.01); *A63B 2220/50* (2013.01); *A63B 2225/096* (2013.01); *A63B 2225/15* (2013.01); *A63B 2225/20* (2013.01); *A63B 2225/50* (2013.01); *A63B 2225/54* (2013.01); *A63C 2203/20* (2013.01); *B33Y 80/00* (2014.12)

(58) Field of Classification Search
CPC ....... A63B 59/50; A63B 24/0062; A63B 5/06; A63B 22/0056; A63B 71/0622; A63B 21/026; A63B 21/0442; A63B 23/03541; A63B 23/1209; A63B 49/02; A63B 53/10; A63B 21/00072; A63B 21/00069; A63B 21/4023; A63B 59/70; A63B 2220/40; A63B 2071/027; A63B 2071/0694; A63B 2209/02; A63B 2210/50; A63B 2220/24; A63B 22/02; A63B 2220/50; A63B 2225/096; A63B 2225/15; A63B 2225/20; A63B 2225/50; A63B 2225/54; A63B 22/0605; A63B 22/0664; A63B 2102/24; A63B 21/0004; A01K 87/00; A61F 5/0123; A01D 7/06; B33Y 80/00; A63C 2203/20; A63C 5/07

See application file for complete search history.

(56) References Cited

U.S. PATENT DOCUMENTS

| | | | |
|---|---|---|---|
| 3,834,696 A | 9/1974 | Spector | |
| 3,944,221 A | 3/1976 | Berkestad | |
| 3,966,655 A | 6/1976 | Kovacs et al. | |
| 4,072,309 A | 2/1978 | Wilson | |
| 4,148,479 A | 4/1979 | Spector | |
| 4,333,645 A | 6/1982 | Wu | |
| 4,620,704 A | 11/1986 | Shifferaw | |
| 4,725,057 A | 2/1988 | Shifferaw | |
| 5,478,075 A * | 12/1995 | Saia ....... | A63B 53/00 473/238 |
| 5,575,722 A * | 11/1996 | Saia ....... | A63B 53/00 473/300 |
| 5,603,678 A | 2/1997 | Wilson | |
| 6,113,508 A * | 9/2000 | Locarno ...... | A63B 60/26 473/516 |
| 6,168,534 B1 * | 1/2001 | Schultz ....... | A63B 53/02 473/299 |
| 6,257,997 B1 * | 7/2001 | Doble ...... | A01K 87/00 473/516 |
| 6,855,067 B2 | 2/2005 | Solheim | |
| 7,291,100 B2 | 11/2007 | Dodge | |
| 8,758,155 B1 * | 6/2014 | Demkowski ...... | A63B 53/12 473/296 |
| 2003/0027658 A1 * | 2/2003 | Li ......... | A63B 60/00 473/318 |
| 2003/0144072 A1 * | 7/2003 | Thompson ...... | A63B 53/12 473/318 |
| 2005/0261079 A1 * | 11/2005 | Qualizza ...... | A63B 53/14 473/316 |
| 2006/0183563 A1 * | 8/2006 | Nemeckay ...... | A63B 53/10 473/239 |
| 2009/0118031 A1 * | 5/2009 | Qualizza ...... | A63B 53/10 473/318 |
| 2009/0163288 A1 * | 6/2009 | Qualizza ...... | A63B 53/08 473/318 |
| 2013/0109493 A1 * | 5/2013 | Hicks ...... | A63B 53/00 473/318 |
| 2017/0021250 A1 * | 1/2017 | Milleman ...... | A63B 53/10 |
| 2017/0282032 A1 * | 10/2017 | Margoles ...... | A63B 60/24 |

OTHER PUBLICATIONS

"Titleist 910 Drivers, Fairway Metals and Hybrids: Total Performance. Percision Fit.", Sep. 22, 2010, https://www.titleist.com/teamtitleist/b/tourblog/archive/2010/09/2.

* cited by examiner

Type I

Fulcrum Resistance = Hand Positions = A, B, C, D, E, Indicia

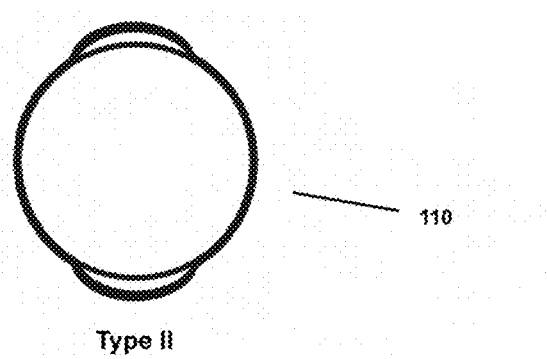
FIG. 1B (a) Type II
FIG. 1B (b)
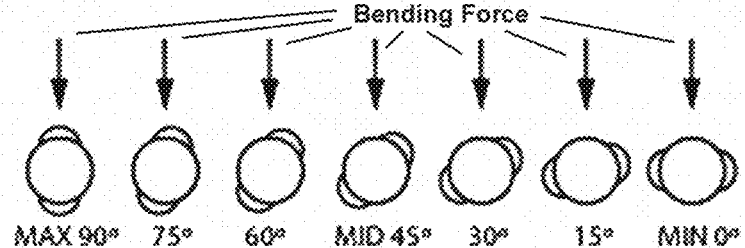
FIG. 1B (c)
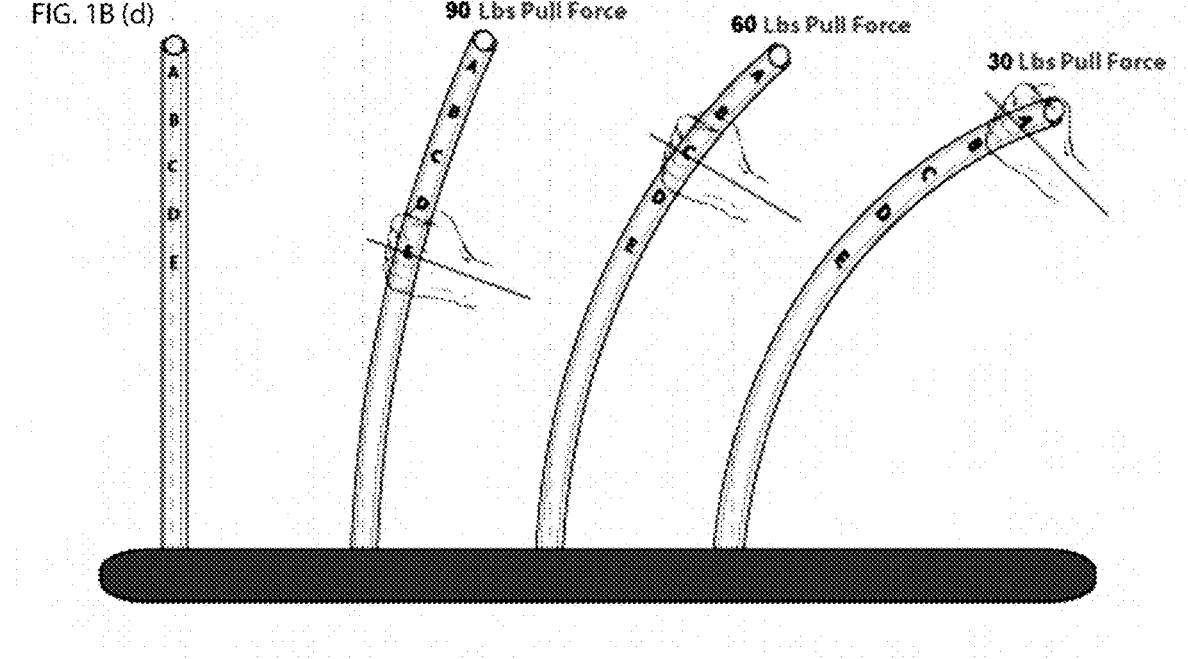
FIG. 1B (d)

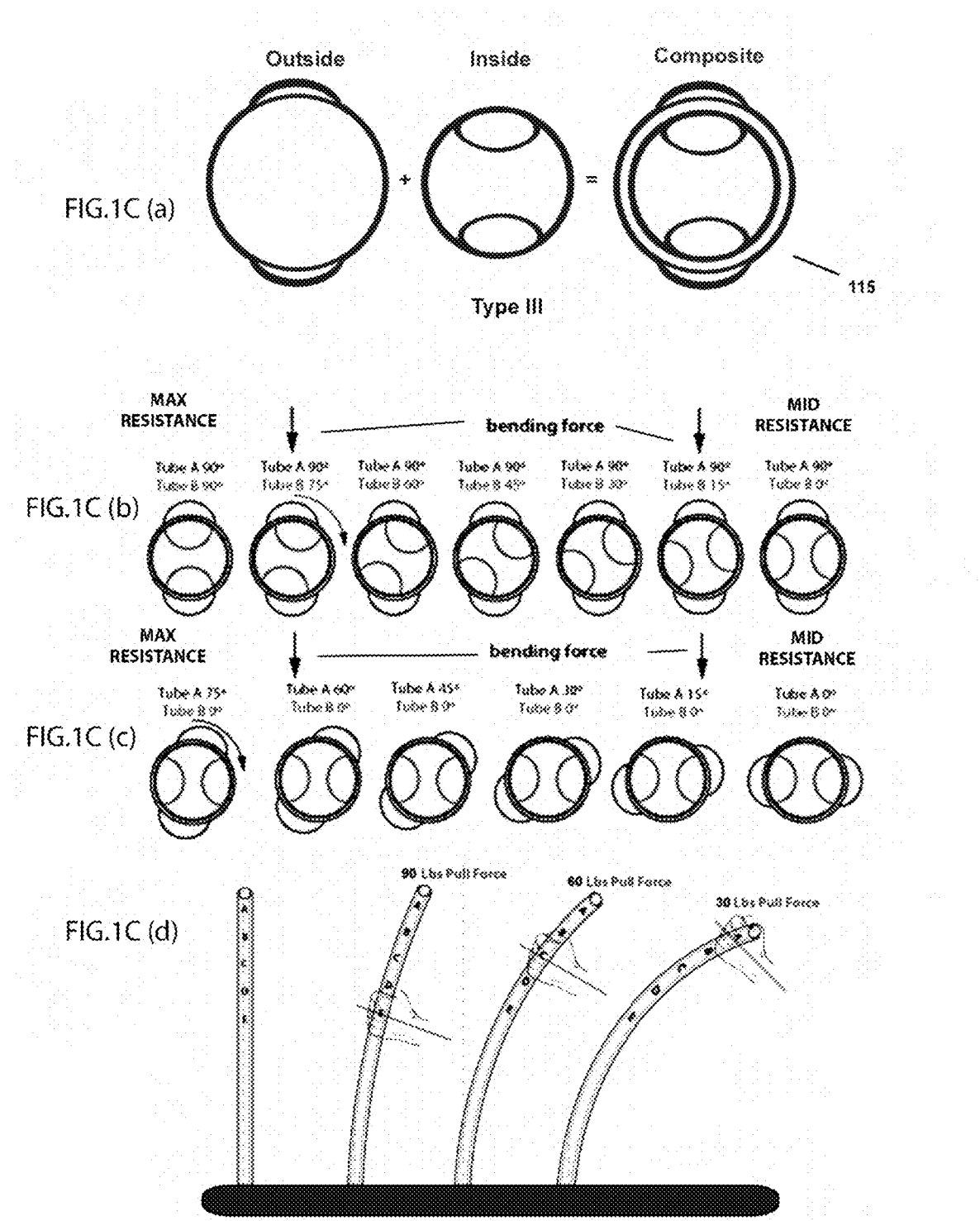

Type V

FIG.1F (a)
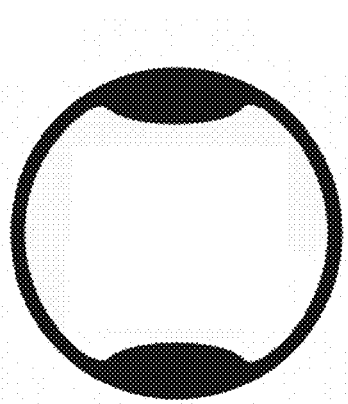
Type VI
MAX Resistance                                                                            MIN Resistance
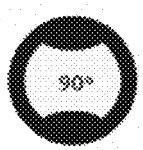 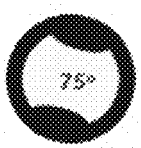  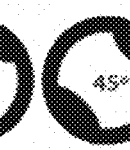  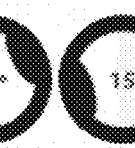 
FIG.1F (b)
Cylindrical Spine Reinforced Beam
FIG.1F (c)
Conical Spine Reinforced Beam
FIG.1F (d)
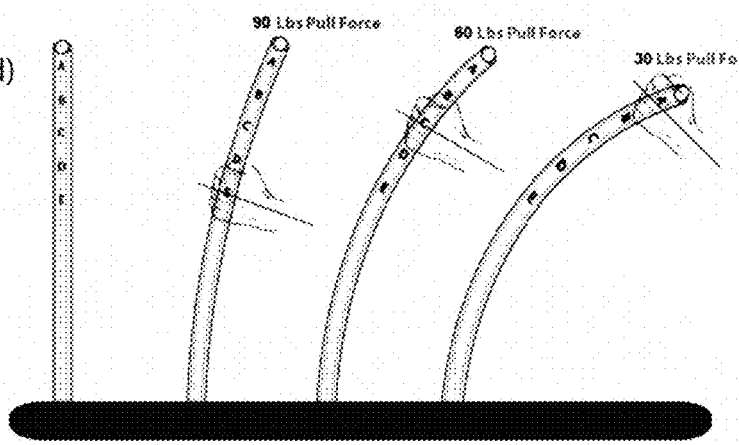

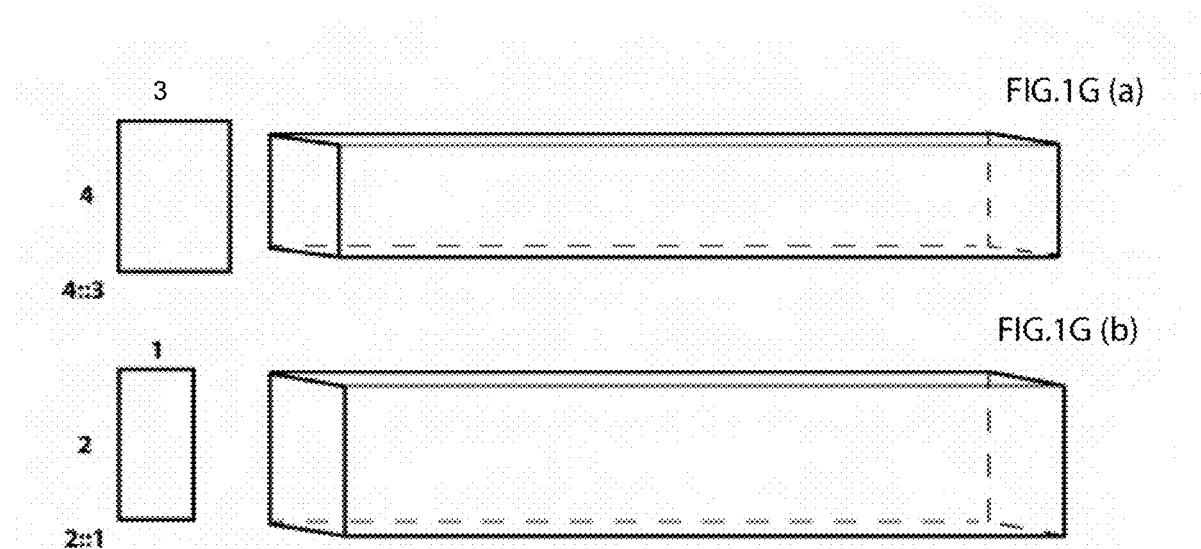
FIG.1G (a)
FIG.1G (b)
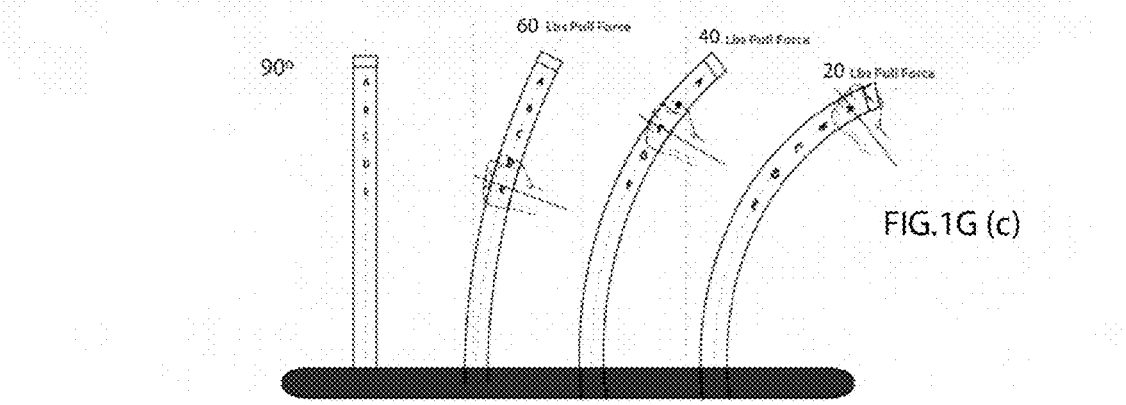
FIG.1G (c)
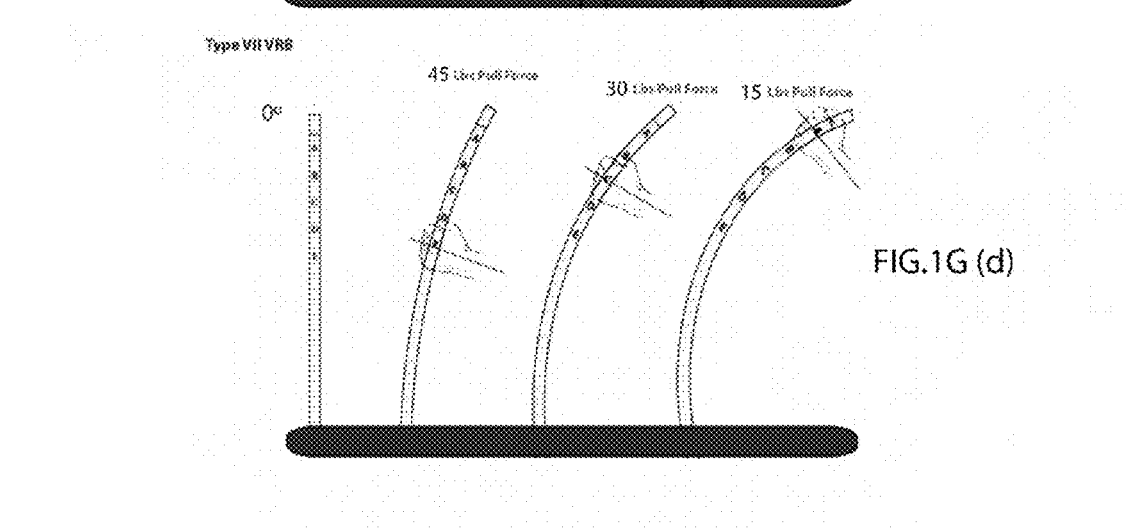
FIG.1G (d)

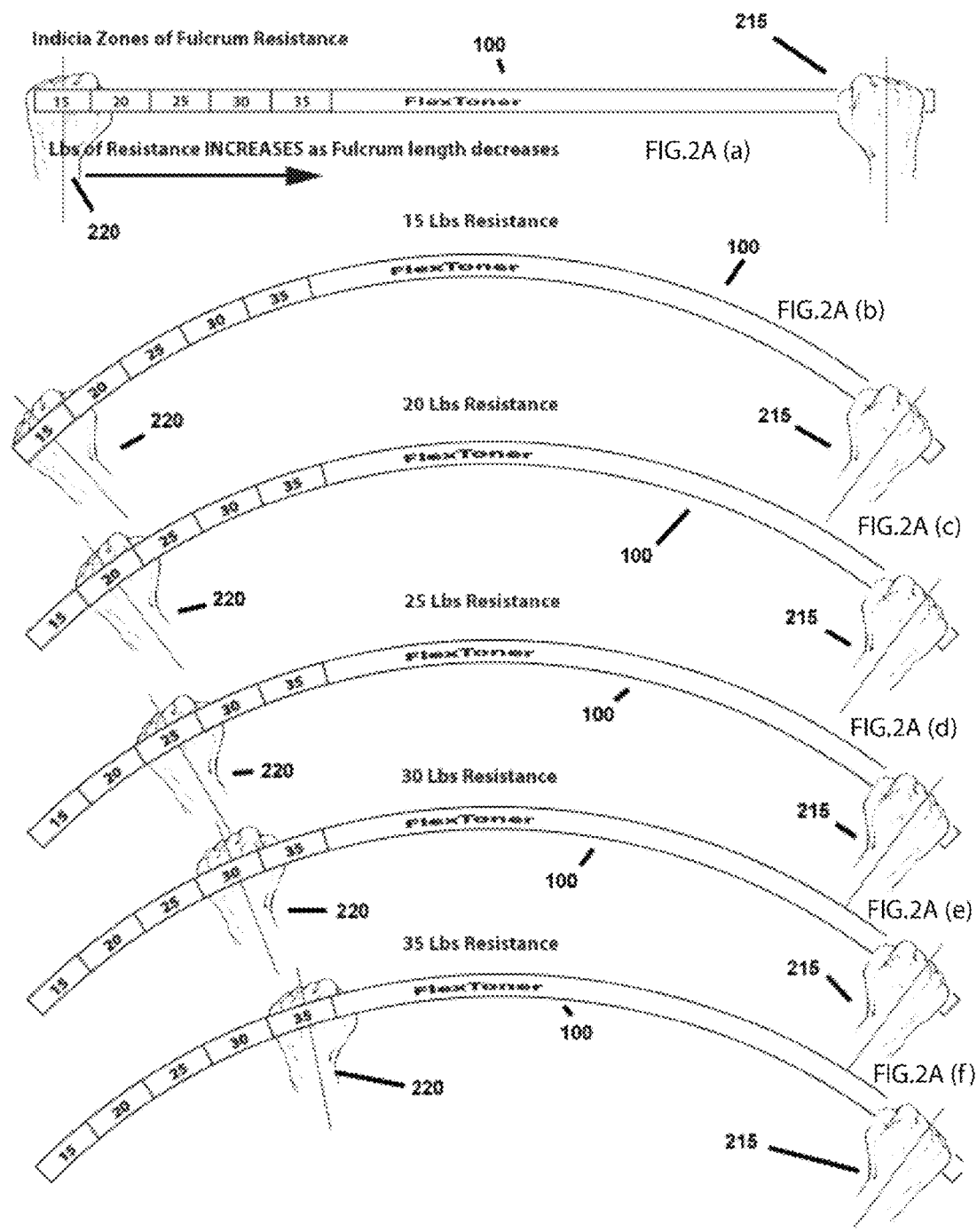

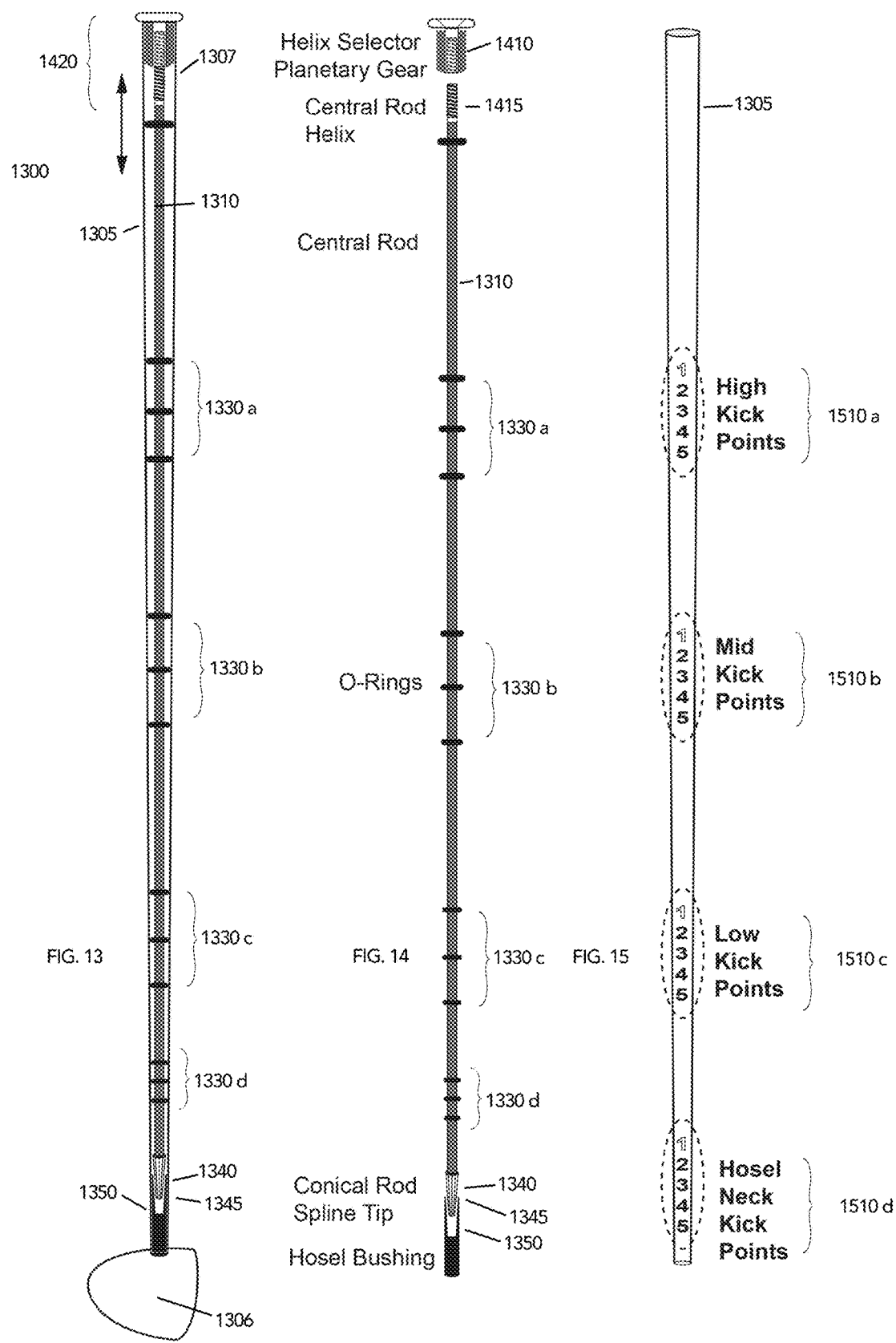

Progressive Bushing
Hosel Deformation
≈
Progressive Hydrostatic
Hosel Shaft Wall Pressure Outer Ring Gear Adjuster Rotates Worm Gear
Helix, Planetary Gear = Select CPM

Planetary Gear Adjuster

METHODS OF ADJUSTING STIFFNESS AND FLEXIBILITY IN DEVICES, APPARATUS AND EQUIPMENT

CLAIM OF PRIORITY

This application claims, pursuant to 35 USC 120, as a Continuation in part, priority to and the benefit of the earlier filing date of that patent application, filed on Dec. 7, 2015 and afforded Ser. No. 14/961,874(U.S. Pat. No. 9,737,747), which claimed, pursuant to 35 USC 120, as a Continuation, of that patent application, filed on Sep. 18, 2012 and afforded Ser. No. 13/622,331(Abandoned), which claimed, pursuant to 35 USC 119, priority to, and the benefit of the earlier filing date of, that patent application filed on Jan. 11, 2012 and afforded Ser. No. 61/585,315, the contents of which is incorporated by reference, herein.

FIELD OF THE INVENTION

The invention relates the field of equipment and more particularly to devices, apparatus and equipment whose degree of stiffness and flexibility may be varied or dynamically controlled.

BACKGROUND

There is a need for varying and adjusting the flexibility and stiffness of associated devices, apparatus and equipment to customize to a user's unique needs, and to the requirements of a particular task or desired outcome.

For example, in recent years, as it relates to the category of sports and fitness equipment, manufacturers and marketers have increasingly turned to different kinds of methods to enhance the customization and performance of sporting and fitness equipment. In some cases, entire lines of sporting equipment have been developed whose stiffness or flexibility characteristics are different from each other and are designed to be matched to the user's unique needs. Such differences, however, may be enough to give the individual equipment user an edge over the competition in that the equipment can be more personally customized, matched to a desired goal, and, therefore, enhance performance.

Until now, the user may choose a particular piece of sporting or fitness equipment having a desired stiffness or flexibility characteristic and, during play, switch to a different piece of sporting equipment that is slightly more flexible or stiffer to suit changing playing conditions or to help compensate for weariness or fatigue or some other anomaly that prevents optimum performance. Such switching, of course, is subject to the availability of different pieces of sporting or fitness equipment from which to choose, at the precise moment the change or adjustment is needed. In many cases, the availability is limited due to cost and over all impracticability.

Additionally, subtle but important changes in the stiffness or flexibility characteristics of sporting or fitness equipment may not be available between different pieces of sporting equipment, because the characteristics may be set by the manufacturer from the choice of materials, design, etc., and to change the characteristics would be impossible, as such customization isn't offered to the user. Further, the user must have the different pieces of sporting equipment nearby during play or they are essentially in practice unavailable to the user.

Thus, it can be seen how the lack of adjustability in stiffness and flexibility may adversely affect optimum performance of a device, apparatus, and equipment.

Turning to additional types of devices, apparatus and equipment, it can be seen how the lack of a practical means of adjustability in stiffness and flexibility may adversely affect performance.

Medical Devices, Apparatus, and Equipment

Medical devices, apparatus and equipment, such as braces that are used for supporting injured limbs, require the flexibility of the device to be adjusted based on the degree of the injury, type of surgery, and the progress of the healing of the injured party. Further, there is a need for on-going protection even after recovery. Yet the degree of adjustability of braces is limited, and, in most cases, fixed. Adjustability of the flexibility of the brace the brace to the specific needs and requirements of the user, may enhance recovery and protection from further injury.

Fitness Devices, Apparatus, and Equipment

Fitness equipment, apparatus and devices require the creation of different amounts of resistance to perform the exercise. For example, with free-weight training the user must change the weight levels to progressively increase the resistance that the user experiences. This often involves the continued and time consuming adjustment of equipment through an exercise cycle and makes changes impractical at best, and at the least a hassle.

Numerous heavy metal plates, large oily machines, weights, rubber bands, and singular resistance rods are the many known forms of fitness training. When the user changes resistance/weight or machine during an exercise set, it is time consuming and interrupts the user's conditioning.

Running Shoes, Training Shoes, Basketball Shoes

The transmission of the shoe wearer's strength (power) from their legs into the ground is directly affected by the sole stiffness of the shoe. Runners may gain more leverage and, thus, more speed by using a stiffer sole. Basketball players may also affect the height of their jumps through the leverage transmitted by the sole of their shoes. If the sole is too stiff, however, the toe-heel flex of the foot is hindered. Thus, athletic shoes are tailored, by the manufacturer, to the particular sport to which the shoe is to be used. In some case, it may be possible for the user to have the ability to tailor the sole stiffness to his/her individual weight, strength, height, running style, and ground conditions. However, this process is performed by the manufacturer and is beyond the ability of the average user. Golf Golf clubs may be formed of graphite, wood, titanium, glass fiber or various types of composites or metal alloys. Each material varies to some degree with respect to stiffness and flexibility. However, golfers generally carry onto the golf course only a predetermined number of golf clubs. Varying the stiffness or flexibility of the golf club is not possible, unless the golfer brings another set of clubs. Nevertheless, it is impractical to carry a large number of golf clubs onto the course, wherein each club having a slight nuance of difference in flexibility and stiffness than another. Golf players prefer taking onto the course a set of clubs that are suited to the player's specific swing type, strength and ability.

The history of golf club shaft design has centered around semi flexible, wooden hickory and later steel golf shafts. The recent design innovation breakthrough of the 1960's using hollow carbon graphite shafts provided a measure of controlled shaft flex with kick points. However, to date there is no mechanical method of selecting or altering shaft flex to enhance or customize performance for the individual golfer.

Essentially golf clubs are sized and fixed to the golfer's swing, speed and body type. This creates inherent and permanently fixed limitations for the equipment, regarding any type of post purchase customization. In essence, a golf club's performance is frozen when the equipment is based upon the mechanical characteristics of the shaft There are currently 5 to 7 industry recognized different fixed shaft flexes: L/W (Lady/Women's), A/I (Soft Regular, Intermediate or Senior), R (Regular), S (Stiff), and X (Tour Stiff, Extra Stiff or Strong). The critical ability to adjust shaft flex would allow the golfer to correct and dial in a slice or hook into a straighter midline fairway shot.

Hockey

Hockey (hockey includes, but is not limited to, ice hockey, street hockey, roller hockey, field hockey and floor hockey) players may require that the flexure of the hockey stick be changed to better assist in the wrist shot or slap shot needed at that particular junction of a game or which the player was better at making.

Younger players may require more flex in the hockey stick due to lack of strength; such flex may mean the difference between the younger player being able to lift the puck or not when making a shot since a stiffer flex in the stick may not allow the player to achieve such lift. In addition, as the younger players ages and increases in strength, the player may desire a stiffer hockey stick, which in accordance with conventional means the hockey player would need to purchase additional hockey stick shafts with the desired stiffness and flexibility characteristics. Indeed, to cover a full range of nuances of differing stiffness and flexibility characteristics, hockey players would have available many different types of hockey sticks. Even so, the hockey player may merely want to make a slight adjustment to the stiffness or flexibility of a hockey stick to improve the nuances of the play; which is not possible with conventional technology Tennis Tennis players also may want some stiffness and/or adjustability in their tennis rackets and to resist unwanted torsional effects caused by the ball striking the strings during play. The torsional effects may be more pronounced in the case where the ball strikes near the rim of the racket rather than the center of the strings.

Lacrosse

Lacrosse players use their lacrosse sticks to scoop up a lacrosse ball and pass the ball to other players or toward the goal. The stiffness or flexibility of the lacrosse stick may affect performance during the game.

Other Racket Sports

Other types of racket sports also suffer from the drawback of being unable to vary the stiffness and/or flexibility of the racket during the course of play to suit the needs of the player at that time, whether those needs arise from weariness, desired held positions, or training for improvement. Such racket sports include racquetball, paddleball, squash, badminton, and court tennis.

For conventional rackets, the stiffness and flexibility is set by the manufacturer and invariable. If the player tires of such characteristics being fixed or otherwise wants to vary the stiffness and flexibility, the only practical recourse is to switch to a different racket whose stiffness and flexibility characteristics better suit the needs of the player at that time.

Skiing, Snowboarding, Snow Skating, Ski-Boarding

Skis are made from a multitude of different types of materials and dimensions, the strength and flexibility of each type differing to a certain extent. Skis include those for downhill, ice skiing, cross-country skiing and water-skiing. For soft snow conditions, the rider may want to have more flexibility so as to allow the board to float. For icier conditions, the rider may want to stiffen the highback to provide greater leverage and power, which results in greater edge control.

Bicycle Shoes

Bicycle specific shoes are rigid and may or may not be attached to bicycle pedals usually through a binding or clip mechanism that prohibits the shoe from slipping off the pedal. The shoe is positioned on the pedal so the ball of the foot is directly over the pedal. The rider's foot flexes as the pedal moves. However, the bicycle shoe is designed for pedaling and walking in these shoes is uncomfortable.

Fishing Rods

Fishing rods are flexed for casting out a line. The whip effect from the casting is affected by the stiffness or flexibility of the rod. Depending upon the fishing conditions and the individual tastes of the user, the user may prefer the rod to be either more flexible or stiffer to optimize the whip effect of the cast and to deal with wind, current, types of fish, and the like. Thus, the user must select the type of flexibility or stiffness when purchasing the fishing rod.

Fins

Diving and swimming fins provide different degrees of stiffness that are fixed, and unchangeable. However, the need to have more flex or less flex and, thus, control fin bend is dependent on the changing conditions. Optimum performance that matches the conditions may be possible with dynamically adjustable fin spine(s). It would also be advantages in that the swimmer/diver would not be unnecessarily fatigued if they had proper matching flex to the conditions.

Sailboating and Sailboarding

Masts of sailboats and sailboards support sails. In many cases the users must adjust the amount of sail that is hanging from the mast according to the weather conditions to prevent damaging the mast caused by stress on the mast.

Canoeing, Rowboating and Kayaking

Paddles for canoes, row boats, and kayaks are subjected to forces as they are stroked through water. The flexibility or stiffness of the paddles, while different depending upon its design and materials, is fixed by the manufacturer. Thus, a rower who desired to change such characteristics would need to switch to a different type of paddle. Carrying a multitude of different types of paddles for use with a canoe, row boat or kayak, however, is generally impractical for the typical rower from the standpoint of cost, bulk and storage.

Lawn Rake

There are times when the flex of a rake's tines are either too flexible or too stiff for the task at hand, be it for raking gardens, light leaf, matted thatch, wet grass, debris. Often the user has to purchase a second rake to accommodate these additional needs.

Hence, there is a need in a plurality of industries, particularly with regard to the golfing industry, in which adjustment of the flexibility or stiffness of a device, apparatus or equipment would be advantageous in a selectable golf shaft that can be adjusted to flex or perform across all the recognized industry flex ranges to compensate and dial in a golfer's variable swing inconsistencies via shaft flex.

SUMMARY OF THE INVENTION

The invention relates to a variable resistance beam or rod that may dynamically control the stiffness and flexibility of devices, apparatus, and equipment. The resilient rods, beams or shafts of solid, semi-solid or hollow construction produce resistance and variable resistances when orientated in a direction of x, y, z plane or combination of planes in 360 degrees of rotation or bending movement.

The variable resistance rod (VRB) technology may be incorporated into different equipment (sports & fitness, lawn, medical, etc.) that require different degrees and direction of stiffness and flexibility, wherein the different degrees of stiffness and flexibility may be controlled in the field in real time by means of a selector, a worm gear, or other mechanical methods to affect a rotated orientation of the variable resistance rods, or by simple hand placement in relation to the fulcrum indicated by an indicia of color, number, symbol or other means.

One aspect of the invention resides in a resilient or resistance rod acting to create variable resistance that incorporates a selectable or adjustable flex resistance by means of hand position and placement.

One aspect of the invention resides in a resilient rod, beam or shaft, including at least one spine, extending substantially the length of the rod, beam or shaft, that provides for variable degrees of flexibility of the rod, shaft or beam depending upon the orientation of the spine with regard to a direction of flex.

One aspect of the invention resides in equipment that adjusts to provide variations in stiffness and flexibility. The equipment may have a rod, beam or shaft with an elongated cavity or rod, an elongated flexure resistance spine, one, two or more locking elements that secure the rod, shaft or beam against rotation at spaced apart locations within the cavity. The rod, shaft or beam is stiffer and less flexible in one direction than in another.

Another aspect of the invention resides in sports equipment that provides variations in stiffness and flexibility. The sports equipment may have an elongated cavity, and a means imparting stiffness and flexibility variations within the cavity so the sports equipment becomes stiffer, and less flexible, in one direction than in another, and one or more locking elements that secure the means against rotation in spaced apart locations within the cavity.

A further aspect of the invention resides in a method of varying stiffness and flexibility, comprising providing equipment (e.g., sports & fitness, medical, footwear & sneakers) having an elongated cavity; imparting stiffness and flexibility variations within the cavity so that the equipment becomes stiffer and less flexible, in one direction than in a different direction; and securing against rotation at least one location within the cavity while imparting stiffness and flexibility variations.

An additional aspect of the invention resides in a resilient shaft or beam acting alone to create variable resistance that incorporates a selectable or adjustable flex resistance by means of varying hand position and placement on the resilient rod in relationship to the fulcrum of the bended rod.

An advantage of the present invention is the ability to provide constant and consistent flex adjustment. This advantage arises from the adjustment being locked in at the ends of the shaft and, depending upon the application, at one or more additional locations through the length of the shaft.

A resilient rod acting alone is also embodied to create resistance that incorporates adjustable flex or resistance by means of hand position and/or specific rotation for means of exercise employing progressive dynamic resistance, which relates to the advantages in exercise of varying degree weight and resistance through a particular cycle.

With regard to a golf club equipment, a selectable, incremental, shaft flex range is achieved by adjusting the height of an internal rod mechanism within the golf shaft via a helix in the grip.

In accordance with the principles of the invention, high, medium and low kick points along the length of the shaft are further flex modified by grouped (internally) O-rings precisely placed along the rod at corresponding kick points. Tangential, internal shaft wall contact of the O-rings correspond to the rod height that is selected within the golf shaft and therefore shaft flex range or CPM.

Shaft flex or CPM is additionally modified via internal compression of the rod into an elastomeric bushing located in the hosel or neck. As would be known in the art, the hosel represents a socket in the head of a golf club into which the shaft is inserted.

In accordance with the principles of the invention, the tangential contact of the O-rings, produces two very beneficial and incremental performance effects upon the shaft; first: tension is progressively increased with corresponding shaft rigidity and second: Anti-head rotation from hydrostatic pressure of the bushing pushing against the internal walls of the hosel, affording greater control and short accuracy.

BRIEF DESCRIPTION OF THE DRAWINGS

The advantages, nature, and various additional features of the invention will appear more fully upon consideration of the illustrative embodiments to be described in detail in connection with accompanying drawings wherein like reference numerals are used to identify like element throughout the drawings:

FIG. 1(a) represents a Type I I-beam configuration that is substantially circular;

FIG. 1A, shown as FIG. 1A(a)-FIG. 1A(c), represents a Type I Non-I-Beam configuration;

FIG. 1B, shown as FIG. 1B(a)-FIG. 1B(d), represents a Type II I-Beam configuration;

FIG. 1C, shown as FIG. 1C(a)-FIG. 1C(d), represents a Type III Dual I-Beam configuration;

FIG. 1D, shown as FIG. 1D(a)-FIG. 1D(d), represents a Type IV Conical beam configuration;

FIG. 1E, shown as FIG. 1E(a)-FIG. 1E(d), represents a Type V Ellipsoidal beam configuration;

FIG. 1F, shown as FIG. 1F(a)-FIG. 1F(d), represents a Type VI Internal 'I-beam' configuration; and FIG. 1G, shown as FIG. 1G(a)-FIG. 1G(d), represents a Type VII Rectangular beam configuration.

FIGS. 1A(a)-(c) through FIGS. 1G(a)-(d) illustrate examples of the resilient rods in accordance with other aspect of the embodiment of the invention as shown in FIG. 1.

FIG. 2A, shown as FIG. 2A(a)-FIG. 2A(f), Illustrates a comparison of a symmetric or basically round and or an asymmetric or elongated cross sectional rod held at two positions.

FIG. 13 illustrates an exemplary golf club device configured in accordance with the principles of the invention.

FIG. 14 illustrates the component parts of the exemplary golf club device shown in FIG. 13.

FIG. 15 illustrates exemplary flex points associated with the device shown in FIG. 13.

FIG. 17A illustrates an expanded view of the first exemplary configuration of the O-ring configuration shown in FIG. 17.

FIG. 18A illustrates an expanded view of the second exemplary configuration of the O-ring configuration shown in FIG. 18.

It is to be understood that the figures and descriptions of the present invention described herein have been simplified to illustrate the elements that are relevant for a clear understanding of the present invention, while eliminating, for purposes of clarity many other elements. However, because these elements are well-known in the art, and because they do not facilitate a better understanding of the present invention, a discussion of such elements is not provided herein. The disclosure herein is also directed to variations and modifications known to those skilled in the art.

DETAILED DESCRIPTION OF THE INVENTION

The object of the present invention is to adjust the flexibility and thereby the resistance of a rod by hand positioning in relationship to the fulcrum of rod; or by bending a rod and spine within the shaft; or by bending a single solid rod; or both the bending of an outer beam and an inner beam in another example. This affects the longitudinal flex and the kick or hinge point of flexure where maximum flexure bending forces arise, depending on the hand position or anchor point in relationship to the fulcrum.

A shaft includes any tube-like structure by itself, attached to the outside of another surface or incorporated within a structure. Examples of a tube-like shaft by itself include hockey sticks, golf clubs, lacrosse sticks, pole vaulting poles, fishing rods, sailboard/sailboard masts, canoe/kayak paddles or oars, baseball bats, archery bows, tennis racquets and exercise machine tensioning rods. Examples of products to which a tube-like shaft might be attached externally include skis, snowboard bindings and bicycle frames.

A beam or rod includes any solid, semi-solid or hollow elongated structure or rod, wherein the rigidity of the beam or rod is dependent at least upon the thickness of the material constructing the beam and the type of material. In the case of hollow beams or rods, the rigidity of the beam is also dependent upon the thickness of the wall forming the beam or rods and the material constructing the wall.

A spine includes any longitudinal structure whose flexure is different in one plane than another, in any increment of 0 to 90 degrees. This can be achieved using many materials. Examples of design shapes that have this property include, but are not limited to, I-beams, ovals, stars, triangles, rectangles, stacked circles, ellipses, etc. The spine may be solid or hollow in construction and utilize combinations of different materials and material thicknesses to achieve the preferred flexibility profile and characteristics.

Figure 1A:
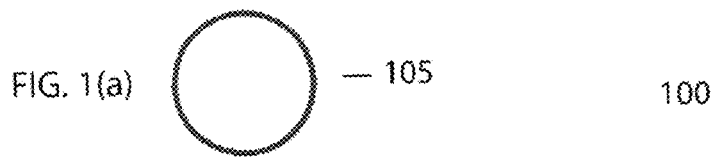
FIG. 1(a)-FIG. (g) represent exemplary views and cross sections of resilient rods, beams or shafts of solid, semi-solid or hollow construction in accordance with a first aspect of the invention that produce resistance and variable resistances when orientated in a direction of x, y, z plane or combination of planes in 360 degrees of rotation or bending movement.
Figure 1B:
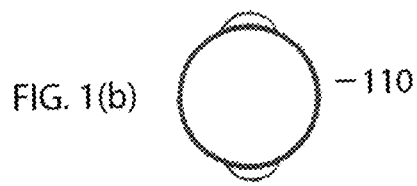
FIG. 1(b) represents a Type II I-Beam configuration that includes a spline.
Figure 1C:
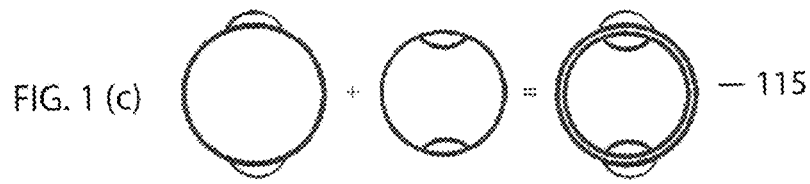
FIG. 1(c) represents a Type III Dual I-Beam configuration that includes an inner and outer spline.
Figure 1D:
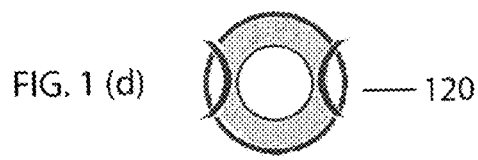
FIG. 1(d) represents a Type IV Conical beam configuration having cut-out section.
Figure 1E:
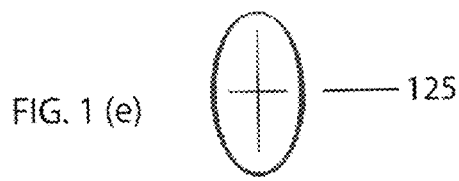
FIG. 1(e) represents a Type V Ellipsoidal beam configuration having a major and minor axis.
Figure 1F:
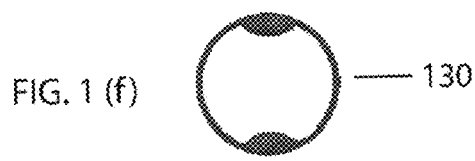
FIG. 1(f) represents a Type VI Internal 'I-beam' configuration having a internal spline.
Figure 1G:
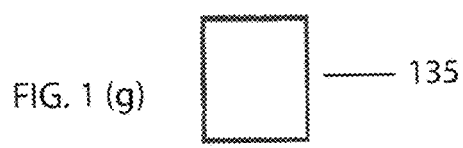
FIG. 1(g) represents a Type VII Rectangular beam configuration.
Figure 1A:
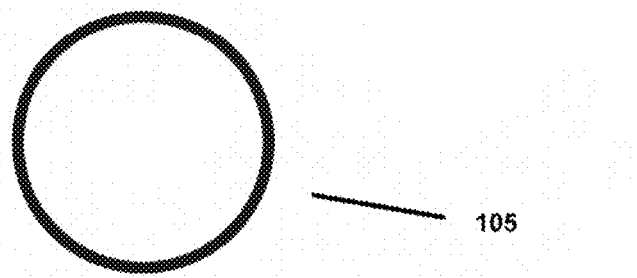
Figure 1A:
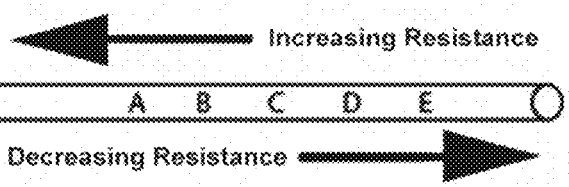
Figure 1A:
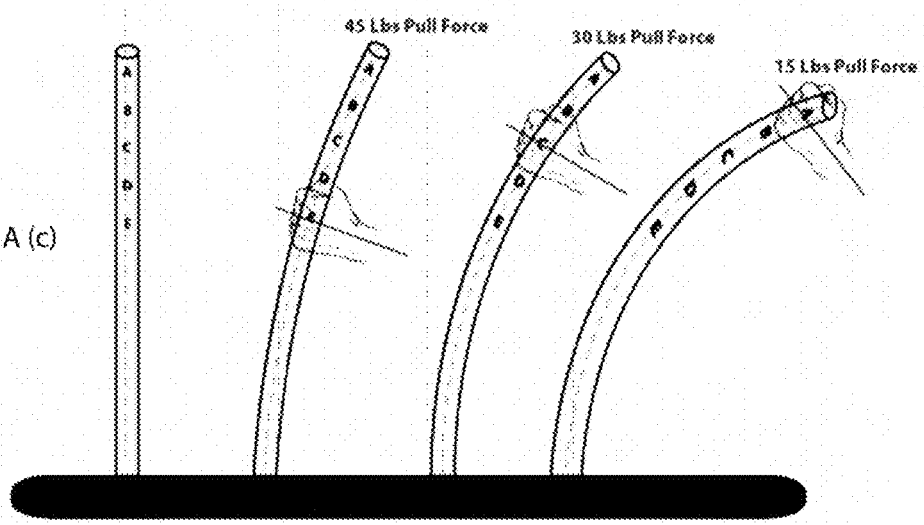
Figure 1D:
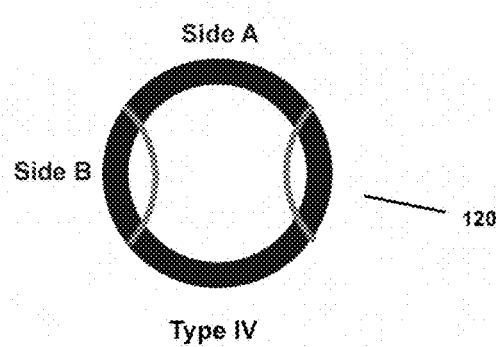
Figure 1D:
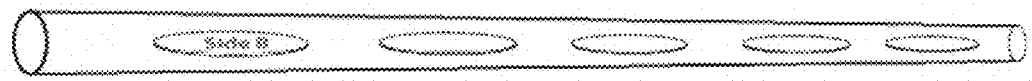
Figure 1D:
Figure 1D:
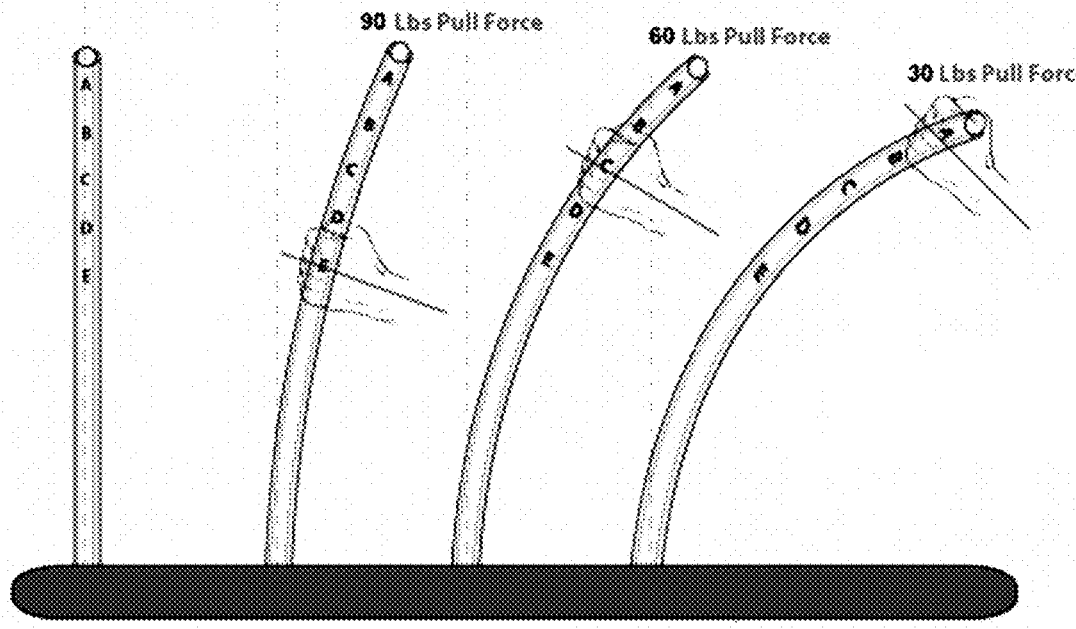
Figure 1E:
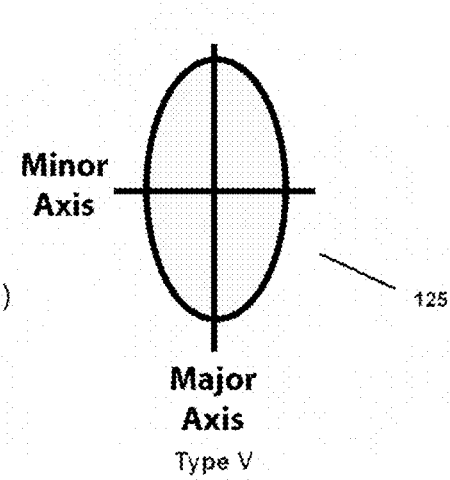
Figure 1E:
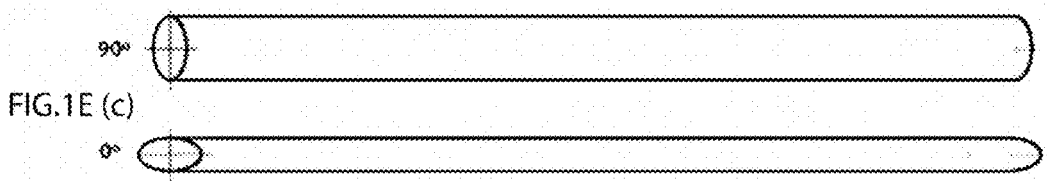
Figure 1E:
Figure 1E:
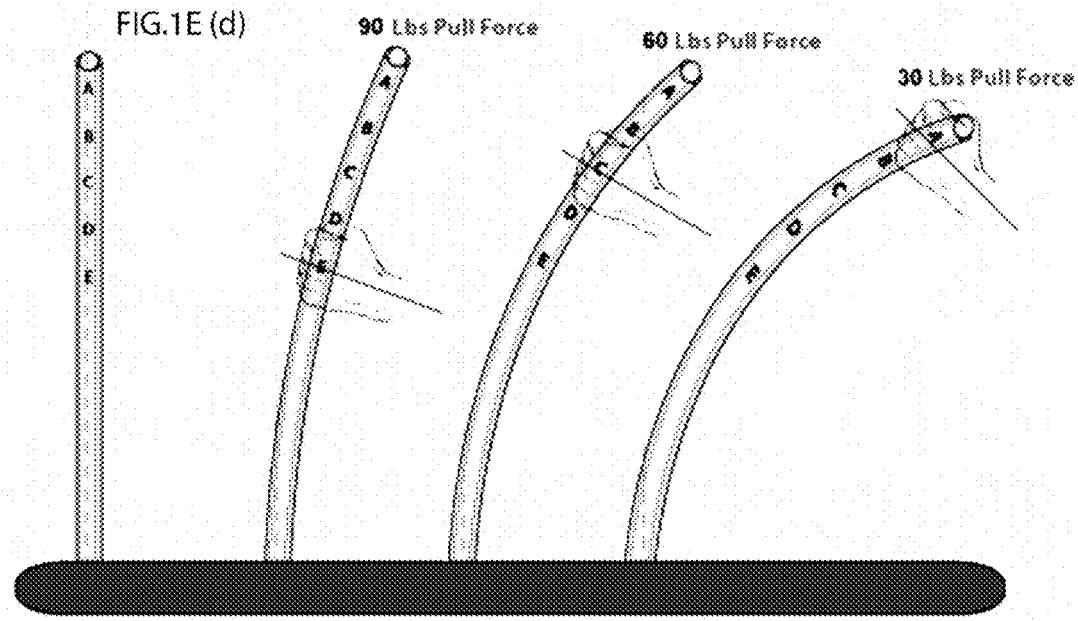

FIG. 1 (a)-FIG. 1(g) represents exemplary views and cross sections of resilient rods, beams or shafts of solid, semi-solid or hollow construction in accordance with embodiment a first aspect of the invention that produce resistance and variable resistances when orientated in a direction of x, y, z plane or combination of planes in 360 degrees of rotation or bending movement.

Type I (FIG. 1(a)): Non-I-Beam: includes a circular cross-section having no outside or internal diameter geometry that would create an i-beam effect: Unlike a single static rod that is intended to produce a single measurement of static resistance, fulcrum adjustable resistance is relative and proportional to hand position as indicated by an indicia zone indicated by graphics, ergonomic ridges, structures, textures and or zones of color.

Type II (FIG. 1(b)): I-Beam includes one of: static outside and/or internal diameter geometry or combination, thereof: I-Beam cross section geometry produces proportional adjustable resistance to rotated orientation: Geometric relationship to resistance.

Type III (FIG. 1(c)): Dual I-Beam: includes rotating inner and outer I-Beam tubes with inner and/or outer geometry or combination thereof to create variable I-beam resistance.

Dual I-Beam cross section geometry rotated produces proportional adjustable resistance to rotated orientation: Geometric relationship to resistance.

Type IV (FIG. 1(d)): Conical beam with hollow, additive or subtractive wall geometry: Conical Beam cross section geometry produces proportional adjustable resistance to rotated orientation: Geometric relationship to resistance.

Type V (FIG. 1(e)): Ellipsoidal beam: solid, semi-solid or hollow beam with or without outside and/or internal diameter geometry or combination, thereof along its major axis generating additional I-beam mechanics and/or subtractive, e.g., conical hollow, geometry along its minor axis. Ellipsoidal beam with a major axis that is wider than the minor axis with or without internal or external geometry along the major axis.

Type VI (FIG. 1(f)): Internal Spine 'I-beam' with one or more spines within a hollow cylindrical or conical shaft.

Type VII (FIG. 1(g)): Rectangular beam with two sides wider than the remaining two sides.

More detail description of the different embodiments of the invention are further illustrated in FIGS. 1A-1G.

FIG. 1A (a)-FIG. 1A(c) illustrate an exemplary embodiment of a type I VRB (variable resistance beam) 100 having a circular cross-sectional area 105. Also illustrated is a series of beams 100 having cross-sectional area 105 that demonstrate the various fulcrum changes through changing hand placement. Each new hand position provides a different resistance such that the resistance increases as a fulcrum length, from a fixed or attached point, decreases, and in the inverse, how resistance decreases as the fulcrum length increases.

FIG. 1B (a)-FIG. 1B(c) illustrate an exemplary embodiment of a type II VRB 100 having a circular cross-sectional area 110 including at least one outer geometric splines 112. Also illustrated is a series of beams 110 with outer geometric spines, demonstrating the various fulcrum changes through hand placement. Each new hand position provides a different resistance. Further illustrated is how the resistance increases as fulcrum length decreases, with respect to a fixed attachment point, and how resistance decreases as the fulcrum length increases.

Also illustrated is a change in the resistance of the VRB 100 having a circular cross-sectional area 110 as the orientation of the outer splines is rotated with respect to a bending force. In this illustrated example, the resistance to the bending force is maximum when the orientation of the outer splines is parallel to the bending force and minimum when the orientation of the outer splines is perpendicular to the bending force.

FIG. 1C(a)-FIG. 1C(c) illustrate an exemplary embodiment of a type III VRB 100 having a cross-sectional area 115 including a combination of an outer shaft having external splines and an inner shaft having internal splines. That is, type III VRB 100 represents a hollow 2-cam cross section. Also illustrated is a series of beams with internal rods or shaft, that have geometric spines, demonstrating the various fulcrum changes through hand placement. Each new hand position provides a different resistance. Further illustrated is how the resistance increases as fulcrum length decreases with respect to a fixed attachment point, and how resistance decreases as the fulcrum length increases. With respect to the fixed attachment point. Also illustrated is a change in the resistance of the type III VRB 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIG. 1D(a)-FIG. 1D(c) illustrate an exemplary embodiment of a type IV VRB 100 wherein at least one elliptical section is removed from the cross section 120. In this illustrative example, the reference Side B represents an area within the type IV VRB 100 that is removed from the VRB. FIG. 1D (b) further illustrates a side view of type IV VRB 100 illustrating the removal of area referred to as Side B from the type IV VRB 100. Also FIG. 1D(c) illustrates is a side view of a type IV VRB 100, that has elliptical scallop cuts along the inner rod or shaft, demonstrating the various fulcrum changes through hand placement. Each new hand position provides a different resistance, wherein the resistance increases as a fulcrum length decreases, and decreases as the fulcrum length increases.

FIG. 1E(a)-FIG. 1E(c) illustrate an exemplary embodiment of a type V VRB 100 having a cross-sectional area 125 comprising a major axis longer than minor axis. That is type V VRB 100 illustrates ellipsoidal beams (hollow or solid) with a major axis longer than minor axis. Also shown is a series of type V VRB 100 demonstrating the various fulcrum changes through hand placement. Each new hand position provides a different resistance. Further illustrated is how the resistance increases as fulcrum length decreases, and how resistance decreases as the fulcrum length increases.

FIG. 1F(a)-FIG. 1F(c) illustrate an exemplary embodiment of a type VI VRB 100 having a cross-sectional area 130 comprising a spine reinforced tubular or conical rod. Also illustrated is a series of type VI VRBs 100 demonstrating the various fulcrum changes through hand placement. Each new hand position provides a different resistance. Further illustrated is how the resistance increases as fulcrum length decreases, and in the inverse, how resistance decreases as the fulcrum length increases.

Also illustrated (FIG. 1F(b)) is a change in the resistance of the type VI VRBs 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

FIG. 1F(c) further illustrates that the type VI VRBs 100 may also be of a cylindrical or a conical shape.

FIG. 1G(a)-FIG. 1G(d) illustrate an exemplary embodiment of a type VII VRB 100 beams having a rectangular cross-section 135. As shown the rectangular cross-section may be sized in different ratios (e.g., 4:3, 2:1) to provide different resistance to bending force. For example, in a case of a 2:1 ratio cross sectional area, the resistance to a bending force applied to the greater side is twice as great at that of the lesser side. The rectangular type VII VRB 100 may be solid or hollow as desired.

Additionally, the resistance rods (VRBs) may include a plurality of graduated indicia that indicate bending resistance by measurement of a fulcrum distance from an anchored position to a hand position[s], as shown.

Thus, in one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand position or fulcrum length.

Figure 2:
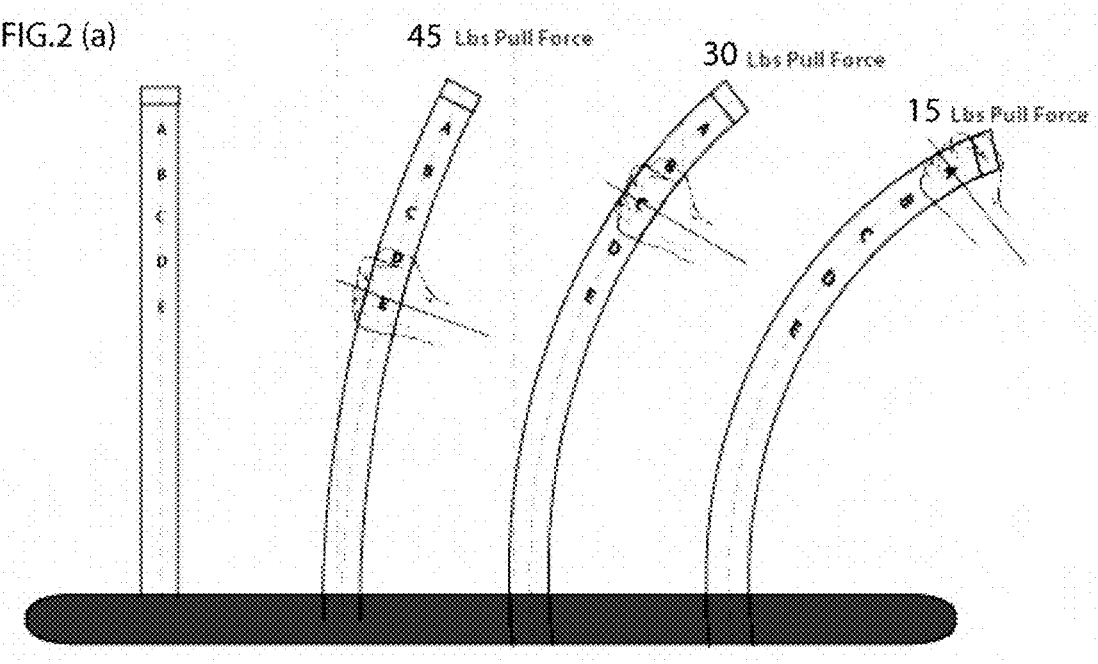
FIG. 2, shown as FIG. 2(a)-(b), illustrates a comparison of a symmetric or basically round and an asymmetric or elongated cross sectional resistances generated by each type of rod with the same hand position indicia.
Figure 2:
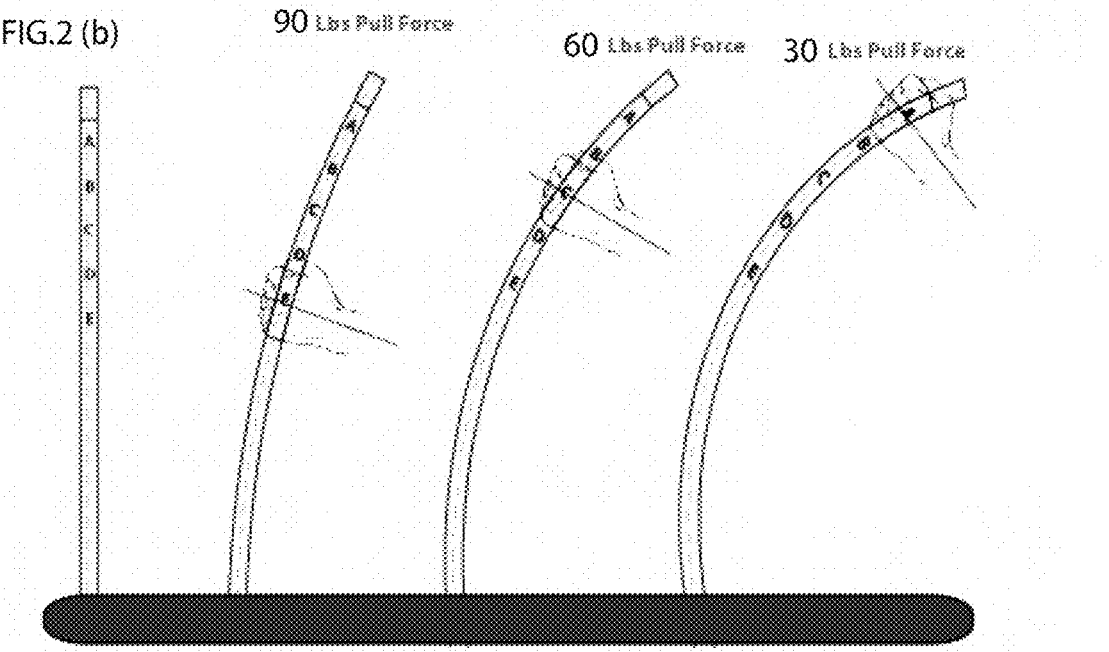

FIG. 2(a)- FIG. 2(b) illustrate the various fulcrum changes through hand placement. Each new hand position provides different resistances. VRB 205 illustrates the variables resistances from a cylindrical beam, rod or bar. VRB 210 illustrates the variable resistances from a type II VRB 100 beam, with added geometric spines, indicating, in this instance, the two-three times increase in pull resistance per identical hand positions along X/Y planes.

Figure 4:
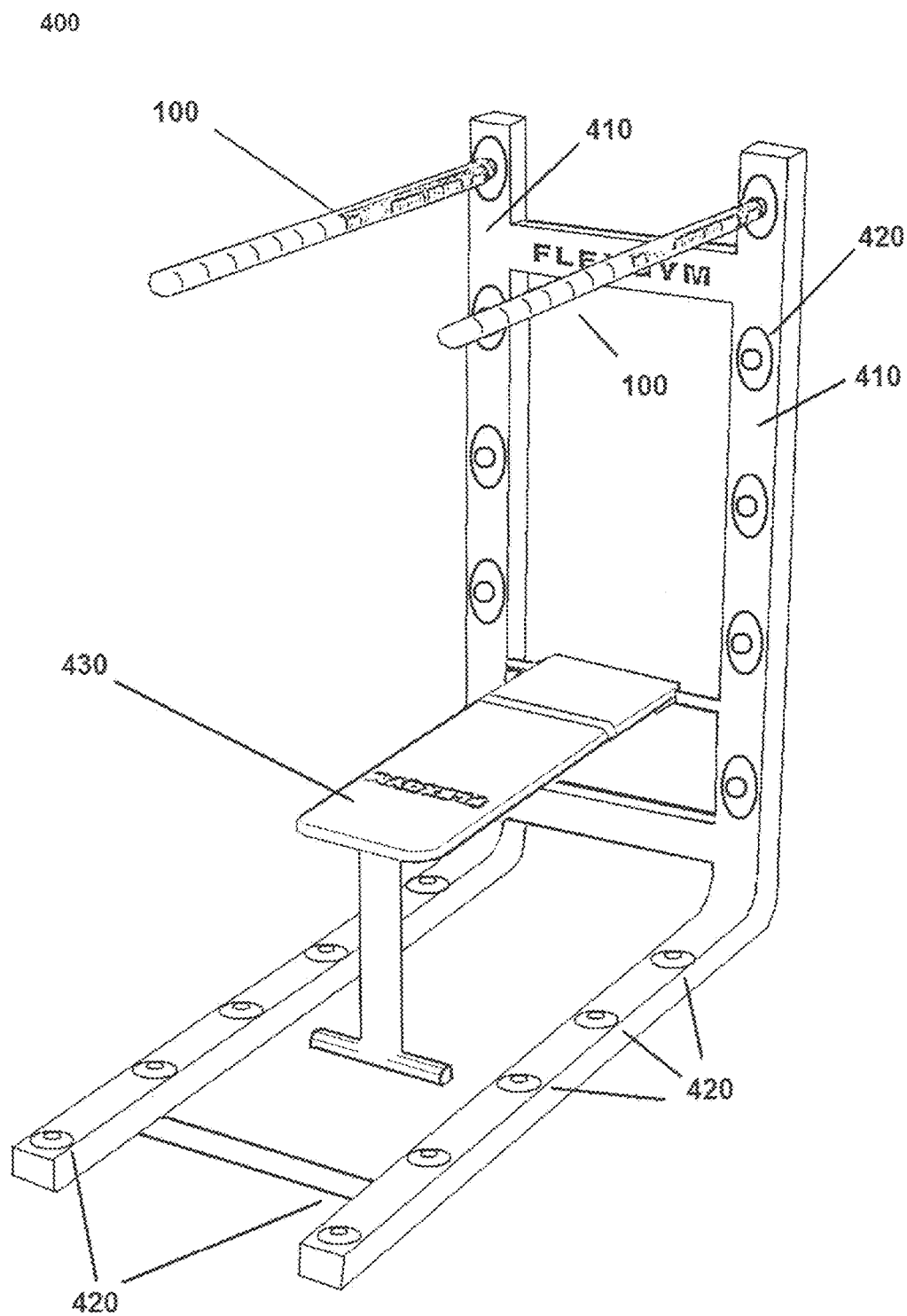
FIG. 4 illustrates an exemplary exercise system configuration in accordance with the principles of the invention that incorporates a plurality of rod holders or anchors affixed along a track or tracks that are designed for the rods to be inserted into and held in place during exercise. The rod holders are designed to increase exercise efficiency by ergonomic utility to facilitate a quick change over of rods that have a higher or lower resistance range.

Table 1 illustrates exemplary resistance levels for different configurations of the VRBs shown in FIG. 1 and 4 for a known material. In this case, resistance levels of VRB of 54 inch length, including 6 grip sections, each grip section being 3 inches for 9/16, 5/8 and 3/4 inch nominal VRBs are determined.

As shown in Table 1, the resistance level increases with the addition of a geometric spine in this example. In addition, by shortening or lengthening the arc length/fulcrum during bending of the beam the resistance may be decreased or increased.

TABLE 1

| Distance from fulcrum | 9/16 inch thick bar | | 5/8 inch thick bar | | 3/4 inch thick bar |
|---|---|---|---|---|---|
| | No Spine | With Spine Min/Max Res | No Spine | With Spine Min/Max Res | No Spine |
| 51 | 7 | 8/15 | 10 | 11/21 | 22 |
| 48 | 8 | 8/16 | 11 | 12/23 | 24 |
| 45 | 9 | 9/18 | 13 | 14/25 | 26 |
| 42 | 10 | 10/20 | 14 | 15/28 | 29 |
| 30 | 11 | 11/22 | 16 | 17/32 | 33 |
| 36 | 12 | 13/26 | 18 | 20/37 | 38 |

Also shown, the resistance level increases as the material thickness increases. In addition, the resistance level increases from a minimum to a maximum value as the orientation of the spine with respect to the direction of the flex increases.

Hence, the resistance level that may be achieved at each hand level depends on the thickness of the VRB and the material composing the VRB. Although not shown it would be recognized that the resistance level may further be based on whether the VRB is hollow. With a hollow VRB, the resistance of the VRB depends on a thickness of the outer wall of the VRB.

FIG. 2A(a)-FIG. 2A(f) illustrate a comparison of a symmetric or basically round and or an asymmetric or elongated cross sectional VRB 100 rod held at two positions. Increasing or decreasing resistance is generated by each rod with a fixed or anchored hand position 215 and a moving hand position 220 into each indicia zone. This distance between fixed hand position and the moving hand position is described as the fulcrum length.

As the fulcrum length or distance between the fixed hand position 215 and the moving hand position 220 increases, the resistance decreases. As the distance between the anchored hand position and the moving hand position decreases, resistance increases.

FIG. 3(a)-FIG. 3(c) illustrates a VRB 100 with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

Figure 3:
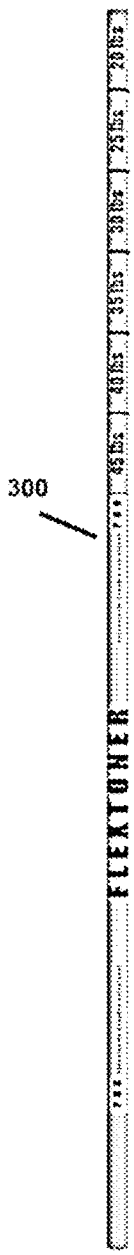
FIG. 3, shown as FIG.3(a)-FIG. 3(c), illustrates a rod with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.
Figure 3:
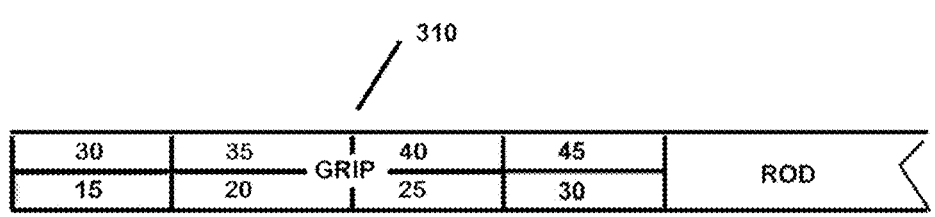
Figure 3:
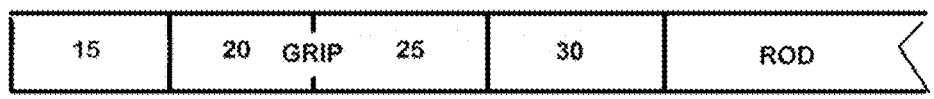

FIG. 3 (a)-(c) illustrate a side view 300 of an exemplary embodiment of a VRB 100 in accordance with the principles of the invention. In this illustrative embodiment, a symmetric VRB 100 may include a plurality of hand positions 315, which indicate one set of resistance ranges in relationship to the fulcrum point. An asymmetric VRB 100, it may include a plurality of hand positions 310, which indicate two sets or multiple levels of resistance ranges in relationship to the fulcrum point and rotated orientation.

FIG. 4 illustrates a view of an exemplary embodiment 400 of an equipment incorporating a VRB 100 in accordance with the principles of the invention. In this illustrative embodiment, a VRB 100 can be inserted into a plurality of insertion points or rod holders 420. The exercise equipment includes a plurality of tracks 410, a plurality of rod holders 420, a bench 430 that may be positioned substantially perpendicular to the plurality of tracks 410 or at an incline angle with respect to the plurality of tracks.

The tracks may be mechanically fixed in vertical or horizontal planes or any combination to maximize rod bend, defined as mechanical work or exercise matched to human proportion or otherwise described as the ergonomic interface.

Figure 5:
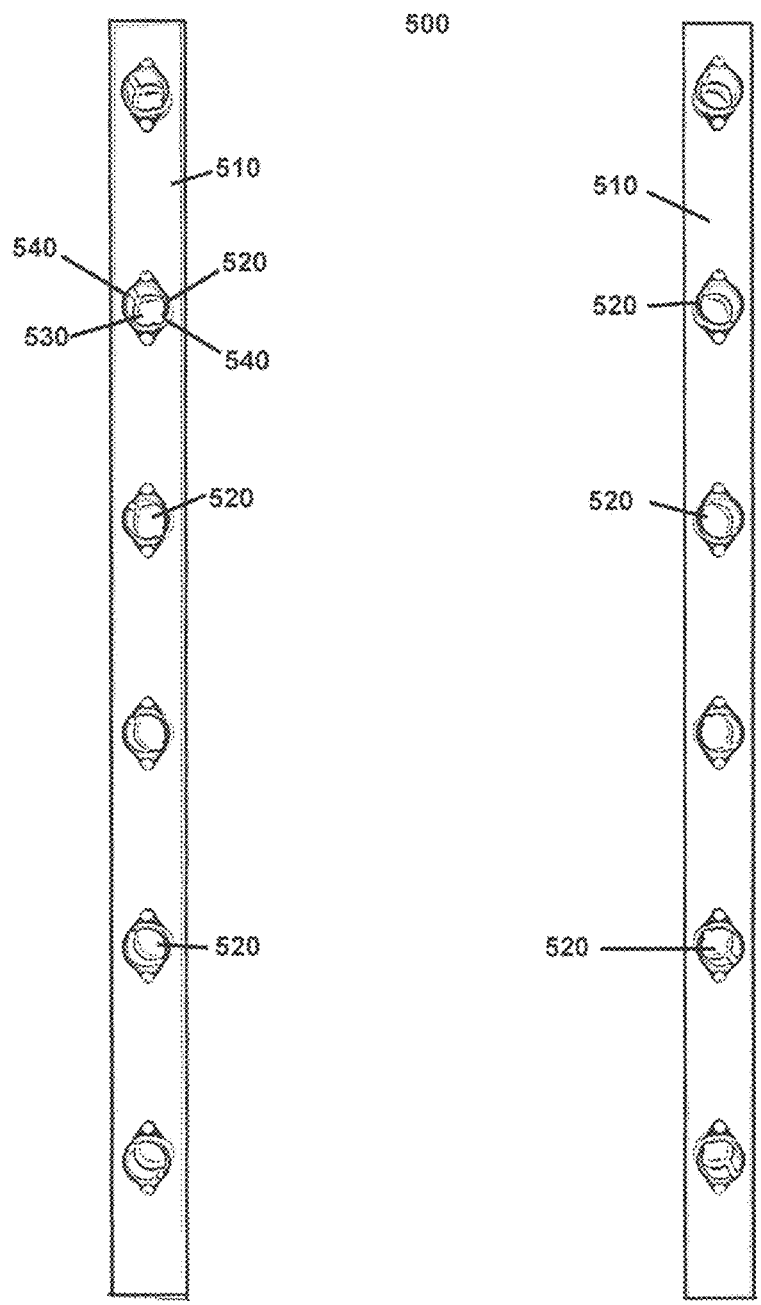
FIG. 5 illustrates an exemplary exercise system configuration of linear rigid tracks affixed with a plurality rod holders designed for the rods to be inserted into and held in place during exercise.

FIG. 5 illustrates a view of an exemplary embodiment of an equipment 500 in accordance with the principles of the invention. In this illustrative embodiment, a VRB 100 can be inserted into a plurality of insertion points. The equipment 510 includes at least one track, which can be wall or floor mounted. Each of the at least one tracks includes rod holders 520. In addition, the walls 530 of the rod holder may be perpendicular or conical with respect to the track 510. Rod holders 520 may further include a stabilizing foot 540 in contact with track 510.

The anchored resistance rod (VRB) generates increased or decreased resistance by anchoring the rod at its base and therefore the user can control the degree of rod bend.

This allows the rod to be used as a dynamic resistance beam for useful exercise. The beam resistance is dependent upon the degree of bend and hand position.

Figure 6:
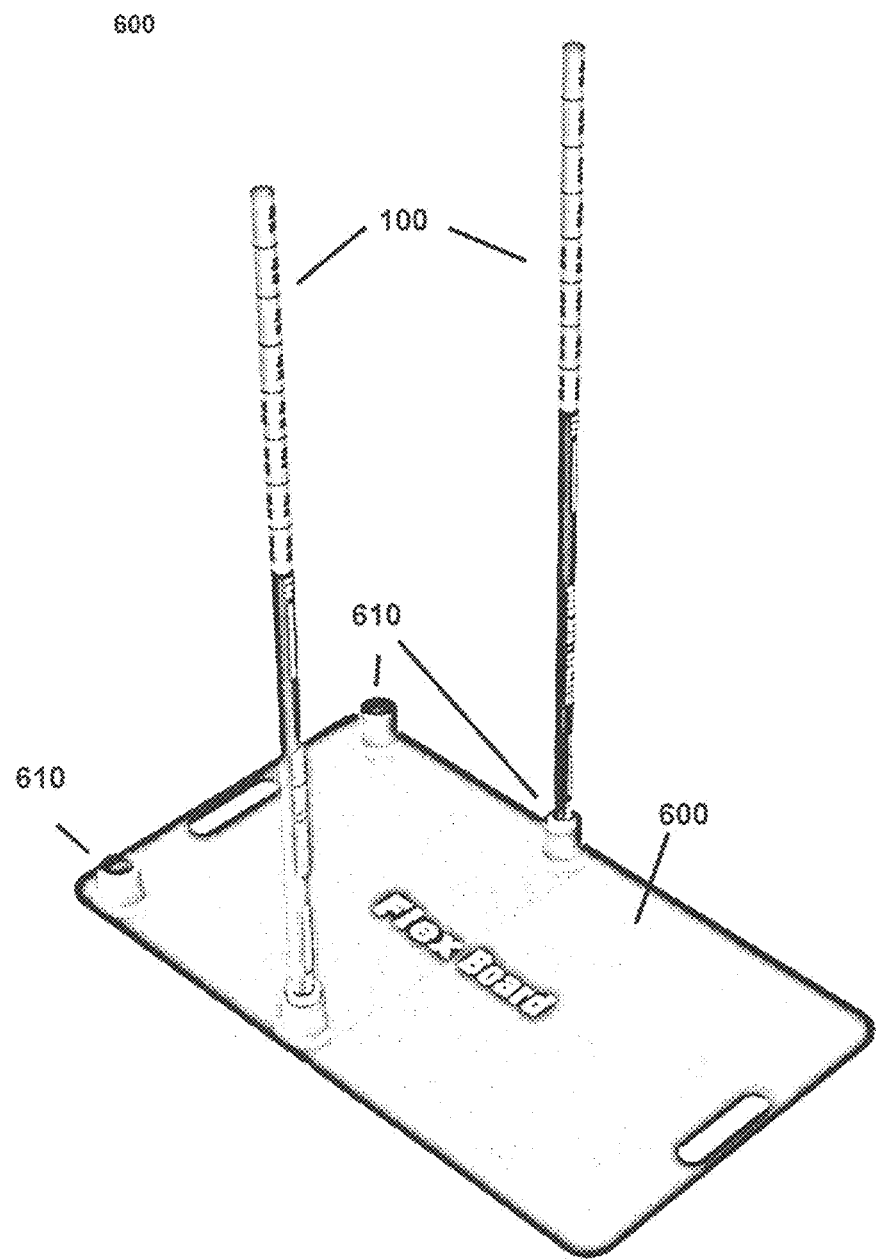
FIG. 6 illustrates an exemplary and portable exercise system configuration in accordance with the principles of the invention comprised of a folding flat workout surface, with a plurality of perpendicular rod holders designed for the rods to be inserted into and held in place during standing exercises.

FIG. 6 illustrates a view of an exemplary equipment 600 in accordance with the principles of the invention. In this illustrative embodiment, a VRB 100 can be inserted into selected ones of a plurality of insertion points 610. In this exemplary embodiment, a plurality of perpendicular rod holders or insertion points 610, similar to those described with regard to FIG. 5, may be incorporated onto a handheld transportable folding workout platform 600.

Figure 7:
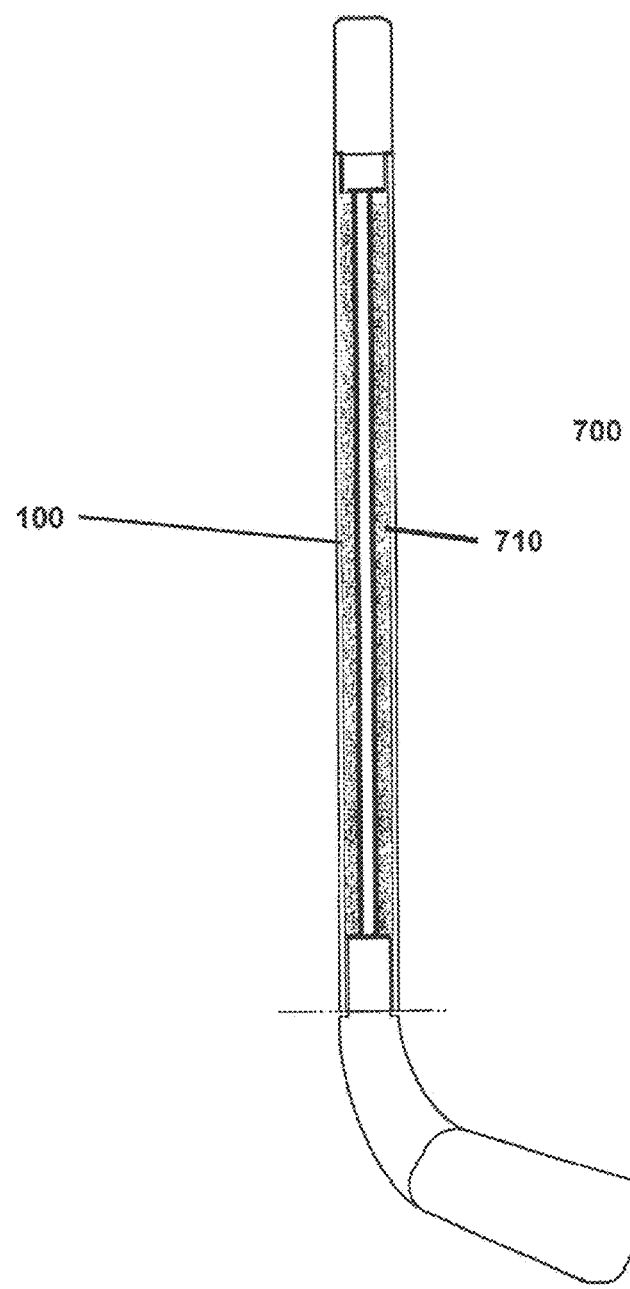
FIG. 7 illustrates an exemplary sports equipment configuration for a resistance beam centrally located within a solid wooden or hollow aluminum or graphite shaft of a hockey stick in accordance with the principles of the invention.

FIG. 7 illustrates a view of an exemplary equipment 700 in accordance with the principles of the invention. In this illustrative embodiment, there is a VRB 100 held in place by foam or other lightweight material 710 within a hollow shaft 720. The position and/or orientation of the VRB 100 within the hollow shaft 720 may determine the stiffness and/or flexibility of the hollow shaft. That is, in the case, a type I VRB 100 is incorporated into the hollow shaft 720, the length of the type I VRB 100 may determine the stiffness of the hollow shaft. On the other hand, if a type II VRB 100 is incorporated into the hollow shaft, then the orientation of the splines to a proposed bending force determines the stiffness and/or flexibility of the hollow shaft 720.

The resistance beam upon manual customized selected rotation imparts greater flexibility or rigidity to the hockey stick by the user, to customize the equipment's response to the user's athletic ability.

Additionally, another method of imparting greater flexibility or rigidity is to raise or lower the resistance beam within the shaft to change the fulcrum or kick point of the stick.

Figure 8:
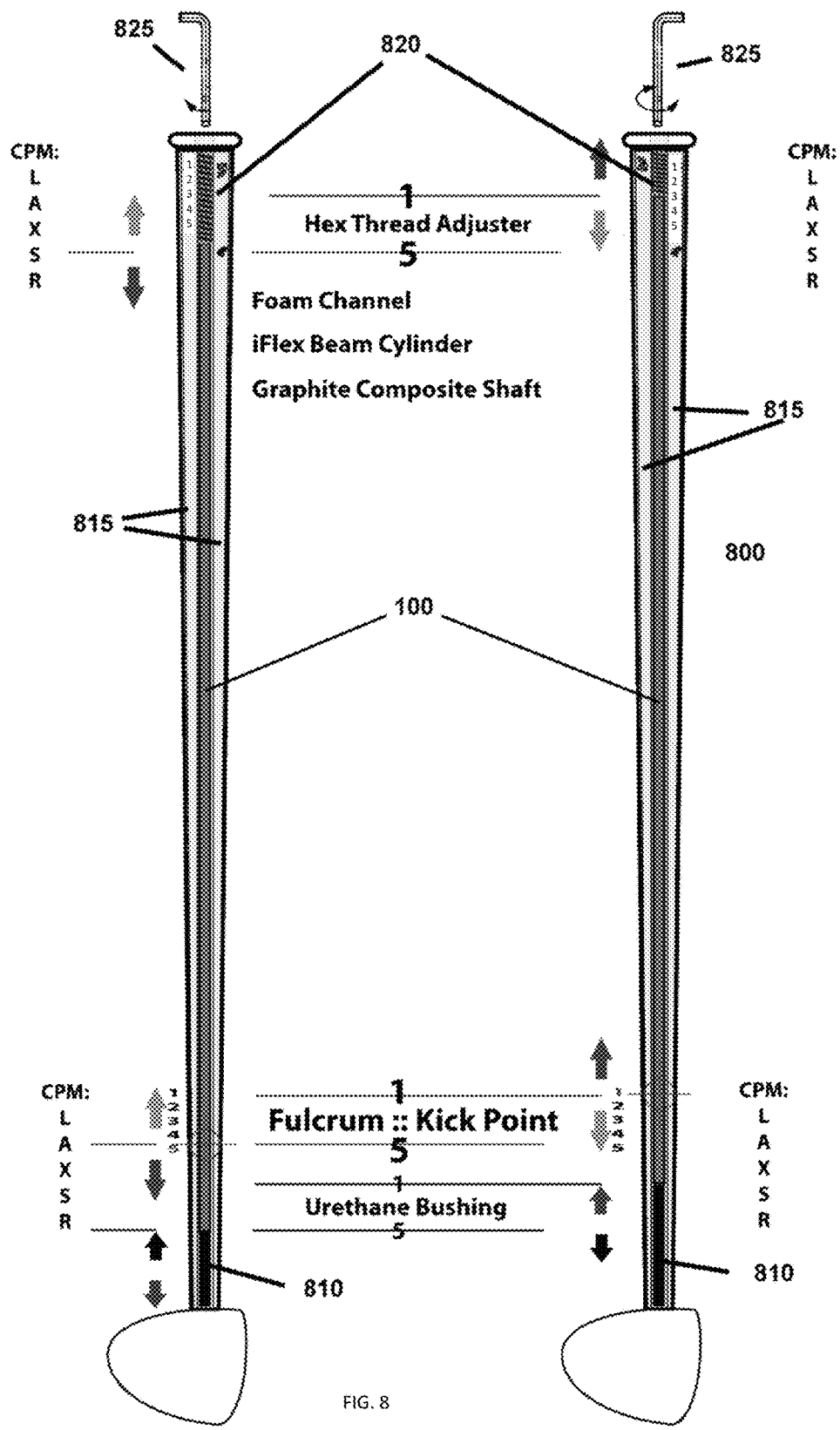
FIG. 8 illustrates an exemplary beam mechanically positioned centrally within a golf shaft configuration in accordance with the principles of the invention.

FIG. 8 illustrates a view of an exemplary embodiment of an equipment 800 in accordance with the principles of the invention. In this illustrative embodiment, an internal VRB 100 is held in position within a hollow shaft by a lightweight material 815, as described with regard to FIG. 7. In addition, one end of the VRB 100 is positioned on a bushing 810 comprising a flexible material such that it may compress or expand as pressure is applied to the bushing 810. In one aspect of the invention, the bushing may be made of an elastomeric material such as a polymer, foam, urethane, rubber, or similar material that may be compressed and returned to an original state when the compressive force is removed. At a second end, the VRB 100 is attached to a means 820 for raising or lowering the VRB within the hollow shaft. The means 820 may be a worm gear type mechanism that raises or lowers the VRB 100, to create a variable shaft flex. The VRB 100 may be lowered by compressing the bushing material 810 and raised by removing the compression pressure from the bushing material 810. Although the means for positioning the VRB 100 is shown as a worm gear that may be turned by an Allen key, it would be recognized that other types of rotating means may be incorporated without altering the scope of the invention. For example, the means for adjustment to alter the position of the VRB 100 may be a screw thread positioned along the outside of the hollow shaft and the turning of a cap on the top of the hollow shaft may lower or raise the VRB 100.

In the illustrated embodiment of the invention shown herein, a VRB 100 rod is centrally raised or lowered within the hollow shaft to increase or decrease flexibility or rigidity of the golf shaft, thereby shifting the kick point or maximum point of flexure up or down the hollow section of the shaft.

Thus, the player or user may select a shaft flex or rigidity range that matches the player's specific swing type, strength and ability.

The 360 degree symmetrical geometry provides a solution for an adjustable golf club and would be fully compliant with the existing USGA (United States Golf Association) rules of golf.

Figure 9:
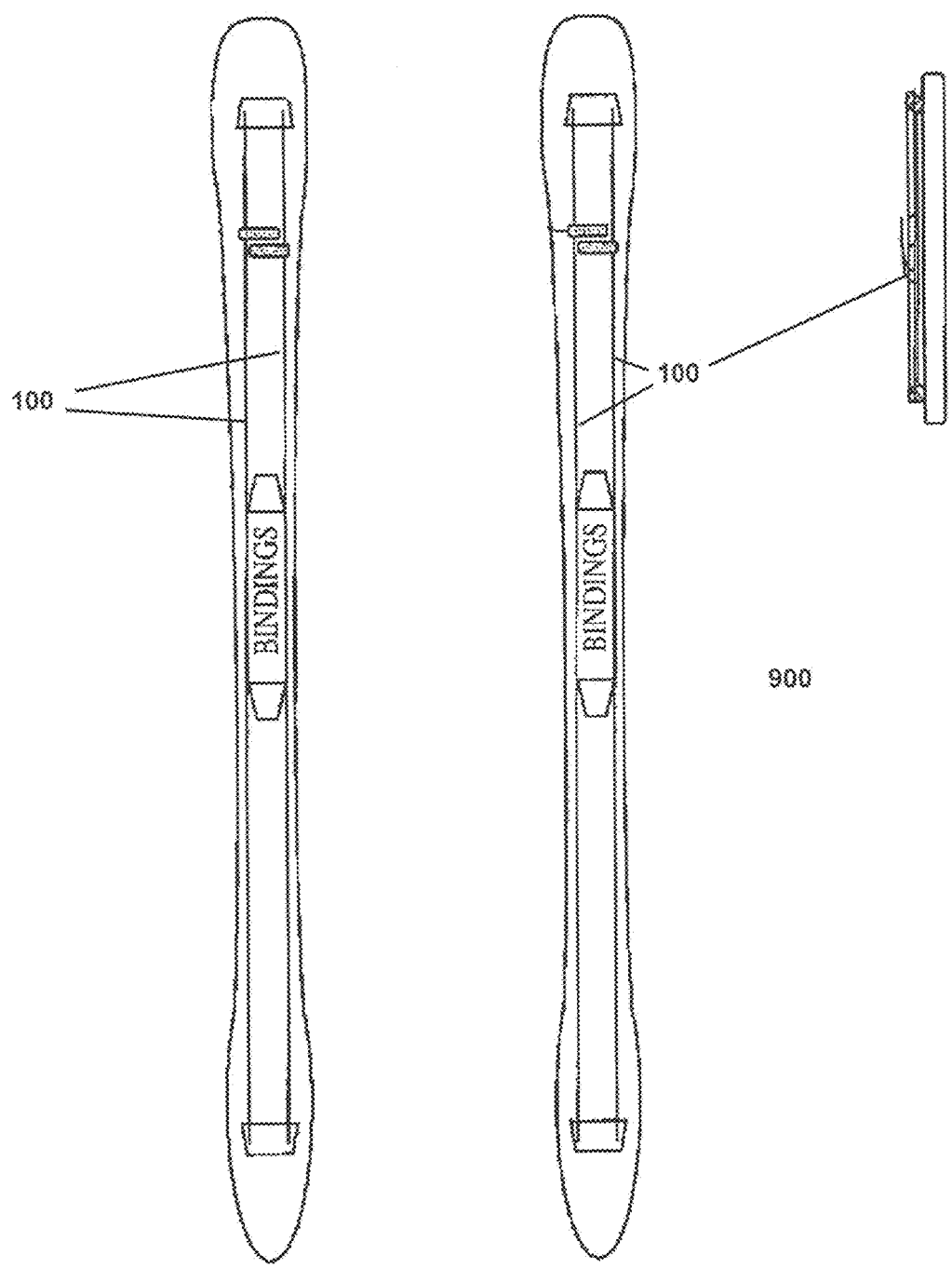
FIG. 9 illustrates an exemplary ski sports equipment configuration with an adjustable resistance beam that imparts a resistance range along the length of the body of the ski in accordance with the principles of the invention.

FIG. 9 illustrates an exemplary ski sports equipment configuration 900 with an adjustable resistance beam VRB 100 that imparts a resistance range along a length of the body of the ski in accordance with the principles of the invention.

The adjustable resistance beam VRB 100 imparts a range of performance characteristics into the ski to match the skier's skill and terrain requirements.

In one application of the VRB described herein, downhill skiing requires a very rigid ski. By adjusting the resistance beam to the highest rigidity setting, the ski will become more rigid with a faster dynamic response when carving turns. A more rigid ski is desirable for icy conditions due to the ability to hold its shape and maintain maximum edge contact with the snow and ice surface.

In another application, mogul skiing over bumps requires a flexible ski. By adjusting the resistance beam to its most flexible setting, the ski will become more conformal to bumps and bend and flex over them.

Thus a terrain adaptable ski is created from a mechanically joined adjustable resistance beam.

The means for positioning the VRB 100 may be similar to that described with regard to FIG. 8.

Figure 10A:
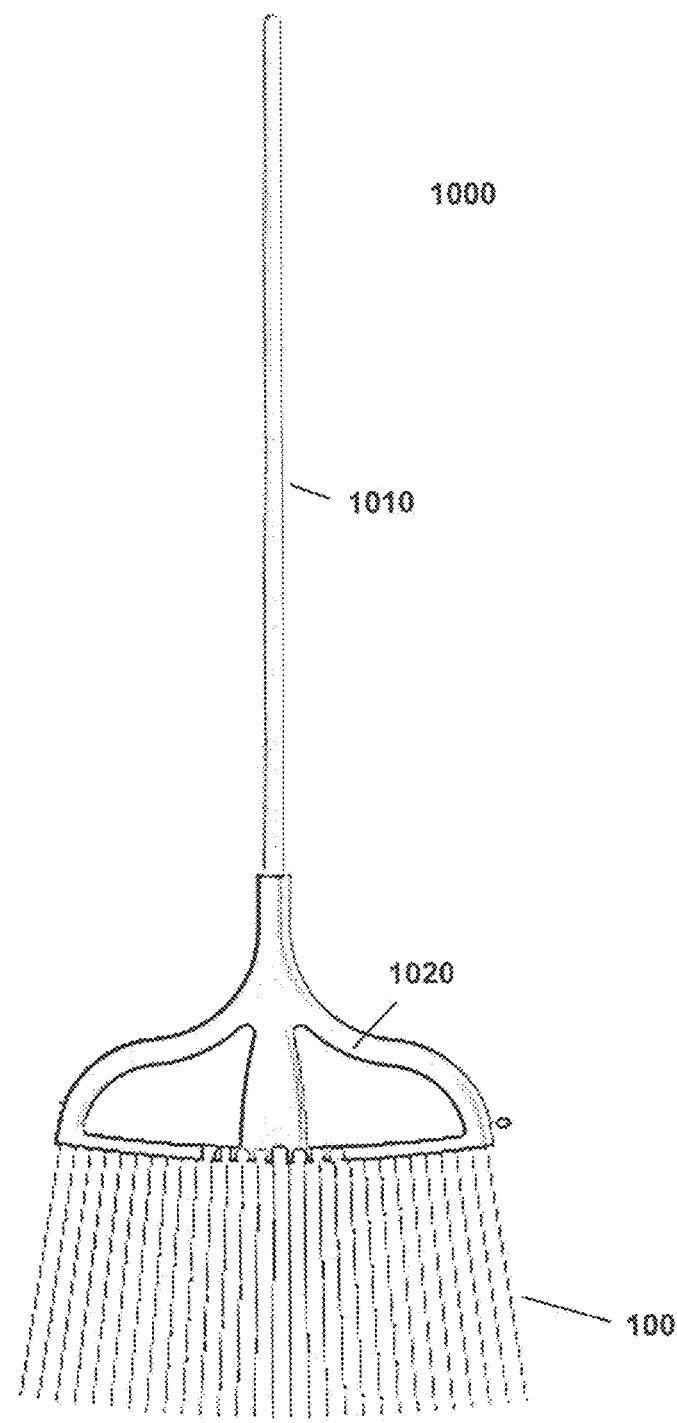
FIGS. 10A-FIG. 10B illustrate exemplary configurations of a lawn device configured in accordance with the principles of the invention. The tines of this adjustable flex rake are individual resistance beams that are simultaneously rotated.

FIG. 10A illustrates a view of an exemplary embodiment of a lawn equipment 1000 in accordance with the principles of the invention. In this illustrative embodiment, tines are individual VRBs 100, and can be simultaneously adjusted to create equal flex in each tine.

Figure 10B:
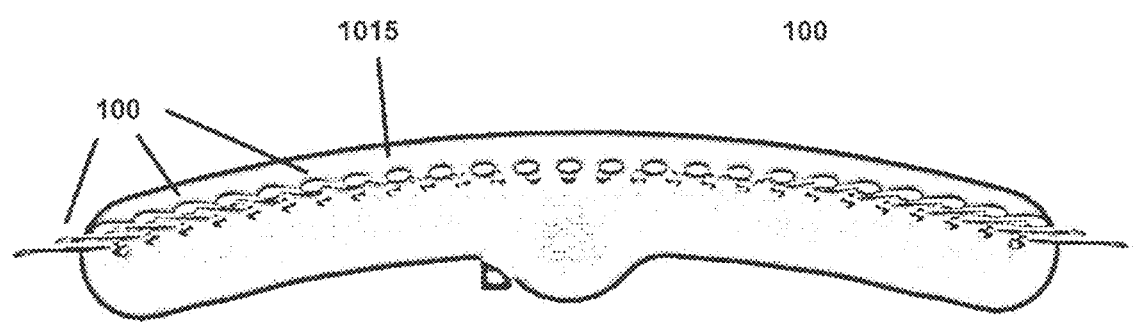

FIG. 10B illustrates a bottom view of an exemplary embodiment of a lawn equipment 1000 in accordance with the principles of the invention. In this illustrative embodiment, the tines VRB 100 may be simultaneously rotated equally to create variable flex.

The rotated tines are locked into an incremental range of resistance positions that are either the most flexible for raking leaves or the most rigid for raking gravel. At the end of each tine is an ellipse that acts a hook dependent upon its rotated orientation.

Figure 11:
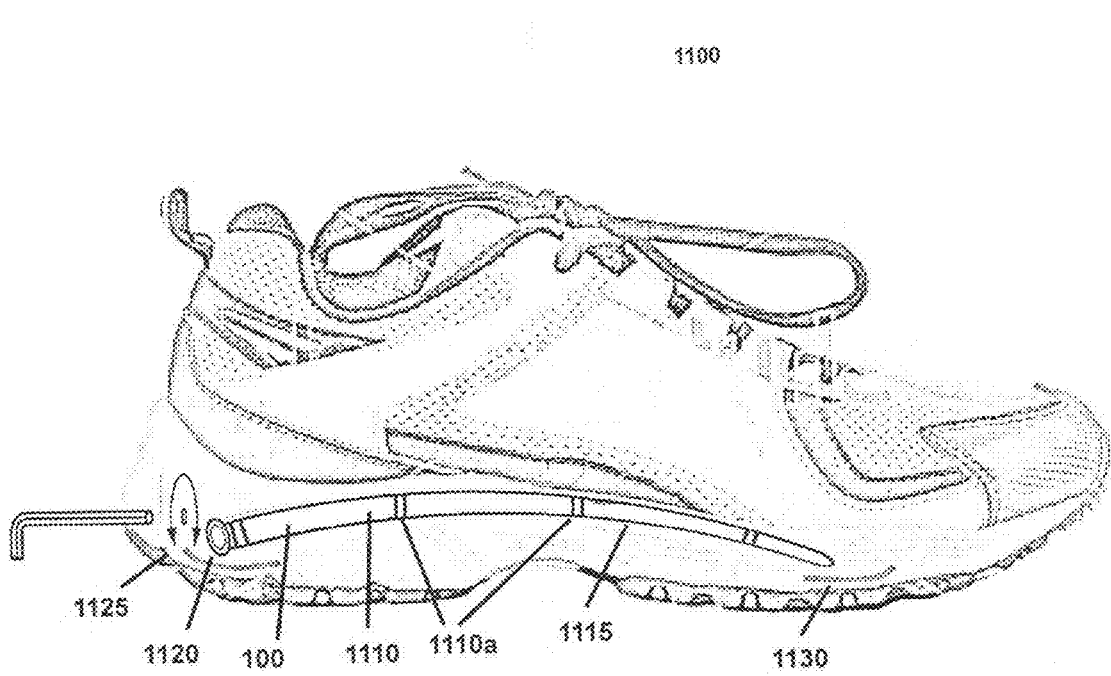
FIG. 11 illustrates an exemplary adjustable active suspension system configuration for sports footwear in accordance with the principles of the invention.

FIG. 11 illustrates a view of an exemplary embodiment of an equipment 1100 in accordance with the principles of the invention. In this illustrative embodiment, internal VRBs 100 are adjusted to create a variable flex. Equipment 1100, which represents an athletic shoe, includes a rubber shoe sole 1115. The athletic shoe 1100 further includes a heel fulcrum 1125 and a toe fulcrum 1130. Between the heel fulcrum 1125 and the toe fulcrum 1130 is an internal cavity 1110. Within cavity 1110 is positioned at least one VRB 100. The VRB 100 includes anti-rollover collars 1110a, which prevent the VRB beam deflection or distortion and are spaced along the VRB 100. The at least one VRB 100 located within the internal cavity 1110 may be adjusted by an adjustment means 1120 that rotates the VRB within cavity 1100. The VRB 100 is further locked in position. The means for positioning the VRB may be similar to that described with regard to FIG. 8.

The transmission of the shoe wearer's strength (power) from their legs into the ground is directly affected by the sole stiffness of the shoe. By employing an adjustable resistance beam as described herein, runners may gain more leverage and, thus more speed, by using a responsive shoe sole customized to their specific requirements.

An adjustable pair of resistance beams within the shoe sole may be insertable, insert molded or structurally connected to the shoe sole in lateral and/or longitudinal positions within the sole and are rotatable to a fixed and mechanically locked position to effect custom flexural resistance range that matches the wearer's optimum performance requirement.

Thus, the resistance beam technology described herein is designed to be a dynamic, adjustable, in-sole suspension system that can absorb the weight of the wearer and release it per each step.

Figure 12:
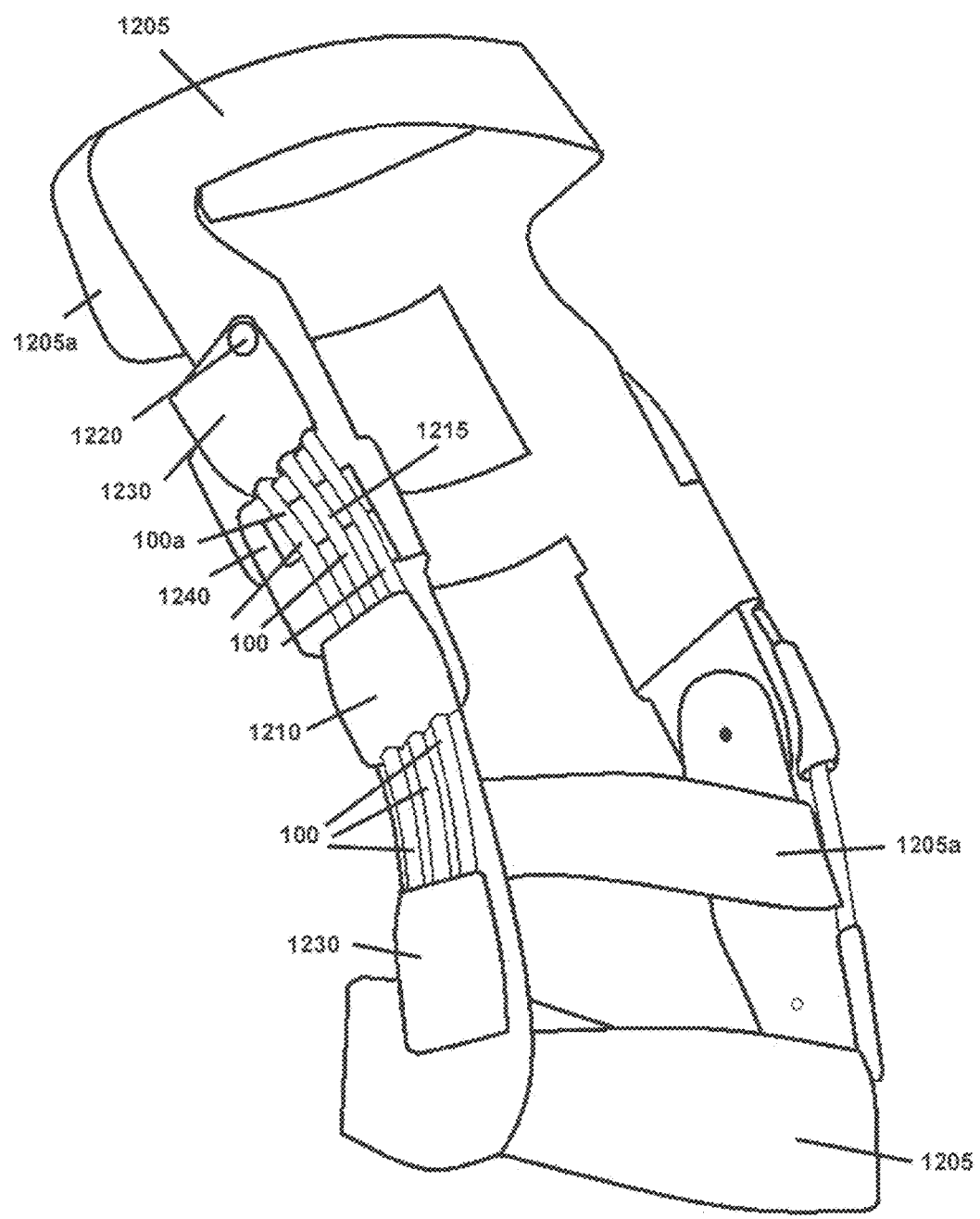
FIG. 12 illustrates an exemplary medical device configured in accordance with the principles of the invention. The resistance beams are employed into mobility assistance and rehabilitative braces that provide dynamic support and suspension via a fulcrum mechanism.

FIG. 12 illustrates an exemplary medical brace in accordance with the principles of the invention. In this illustrative example, at least one VRB 100 is incorporated into a VRB assembly 1215 comprising an anchor 1230, an adjuster 1220, and a fulcrum 1210. The bracing system in FIG. 12 is comprised of a thigh leg strap collar 1205 attached to a frame with a fulcrum 1210 connected to a hinge 1225 with an upper arm 1240 with a bushing piston acting as a second cartilage.

In this illustrative embodiment, VRBs 100 are adjusted to create a variable flex. Element 1205 illustrates leg strap or collar (thigh). Element 1205a illustrates leg strap or collar (calf). Element 1210 illustrates fulcrum for VRB to maintain controlled bending. Element 1215 illustrates a VRB assembly (one or more VRB's) that acts as a leaf-spring/unloader; i.e., a first suspension point. Element 1220 illustrates VRB assembly adjuster to customize flexibility or resistance. The assembly adjuster 1220 may be a worm gear as previously described. Element 1225 illustrates a hinge that mimics the bio-mechanical movement or range of an anatomical joint (e.g. knee). Element 1230 illustrates VRB assembly anchor with spring/bushings: i.e., a secondary suspension point. Element 1240 illustrates a telescoping upper hinge arm with a bushing piston, a second cartilage: i.e., a third dampening or cushioning point. VRB assemblies 100a or 1215 provides a dynamic supportive structure designed to act as an artificial or second knee to support a damaged or injured one.

An additional benefit of incorporating the VRB 100 technology into medical devices is that the resistance rods, under compression, create a proportioned constant vertical lift to unload 1215 and dynamically support the joint (e.g., a knee) during post op, rehabilitation, arthritis or during extreme sports. Hence, the VRB 100 technology described herein provides a truly functional and adjustable brace that provides for Shock Absorbing 1215, 1230, 1240, Active Suspension 1215, Adjustable Comfort DST Unloader Knee Brace.

As previously described, resistance ranges are generated by rotating the beams over a fulcrum positioned adjacent to a body joint.

Dynamic support is also beneficial for the recuperative period following operation, rehabilitation, arthritis or during extreme sports. Additionally, resistance beam assemblies may also contribute to shock absorption via a bushing and piston arm mechanically connected to the beam assembly. Furthermore, beam assemblies positioned on each side of a joint act as lateral stabilizers.

In one aspect of the invention, the VRB's 100 may be composed of thermoplastic polymers, especially high tenacity polymers, include the polyamide resins such as nylon; polyolefin, such as polyethylene, polypropylene, as well as their copolymers, such as ethylene-propylene; polyesters, such as polyethylene terephthalate and the like; vinyl chloride polymers and the like; and polycarbonate resins, and other engineering thermoplastics such as ABS class or any composites using these resins or polymers. The thermoset resins include acrylic polymers, resole resins, epoxy polymers, and the like.

Polymeric materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g. carbon nano-tubes, et al, to fill the molecular gaps, therefore strengthening the material.

Additional materials that the resistance rods or VRB's may also be composed of include high tensile aircraft aluminum and high carbon spring steel and/or high tensile strength to weight materials.

Although the different applications of the VRBs shown herein refer to VRB 100 (type I), it would be recognized that each of the applications may incorporate one or more of the other type of VRBs (i.e., type II through type VII) without altering the scope of the invention.

The resilient VRB's shown in herein may be used with, or in conjunction with, sports equipment and exercise apparatus to create meaningful exercise and or other useful mechanisms. For example, devices suitable for exercise equipment, sports equipment, home improvement and medical mobility may be created to selectable control bending strength or resistance ranges to impart performance benefits. VRB's may be secured at one or more fixed points with the appropriate device may be used to provide appropriate variable resistance. In addition, the VRBs may be handheld at various points along the beam length to affect fulcrum resistance and/or rotated to different incremental orientations to affect resistance with discrete geometric cross sections. In one aspect of the invention, VRB's may be perpendicularly mounted to a variety of mechanical apparatus to affect resistance and may additionally be handheld in the air to expand the exercise envelop.

The VRB's described herein may be manufactured based on a method selected from a group consisting of: rapid prototyping, stereolithography, molding, casting, extrusion and others known in the art.

A VRB, which may be solid, semi-hollow or hollow, with or without geometrically created I-beam effect (i.e., spines) on the outside or interior diameter generates resistance depending on the axis of orientation and/or a fulcrum position has been described herein. A VRB 100, with incorporated I-beam geometry on the outside diameter, can allow for the dynamic adjustment of resistance of the device. An advantage of a device including a VRB described herein may be-compact, lightweight and offer the ability to more easily and quickly change a desired level of resistance than is typically found in units using weights, rubber bands, bows or springs. By simple hand reposition, as shown in FIG. 3, or rotation of beam of the incorporated into the device, a desired resistance level may be achieved. The VRB 100 disclosed, herein, can provide resistance, depending on the orientation of the beam, to the user. In addition, the device can vary the resistance provided to the user during an exercise, without interrupting the exercise cycle. Additional beam resistance is achieved depending upon the relative orientation of the beam within a 180° degree hemisphere of movement relative to the user. Hence, according to the principles of the invention, a progressive dynamic resistance may be achieved with a variation of the orientation of the beam or shaft shown herein.

The principle of Progressive Dynamic Resistance (PDR) are:

controlled and rotatable (variable) resistance beam with ergonomic work zones:

Multiple, sequential, mechanical resistances are achieved for the purpose of rehabilitation and exercising of endo-skeletal musculature.

Increased/decreased incremental mechanical resistance and exercise adjustability is achieved through beam rotation and or fulcrum hand position relative to the beam or arc length/distance along the resistance beam to impart desired work load.

PDR's 180° or 360° degree range of dynamic arcing motion provides an exercise resistance program for every male or female body type with variability in muscle size and strength to provide gain after unilateral resistance training of progressive resistance exercise (PRE).

PDR's incremental mechanical resistance capability (i.e., resistance adjustability through rotation and/or fulcrum hand position) facilitates and customizes the user's strength curve and exercise requirements from simply moving hand/leg position to tailor the optimum resistance to maximize the workout of the targeted muscle group.

PDR resistance beam technology does not have mechanical flat spots or dead spots and provides continuous resistance curve to maximize workout loading on the targeted muscle groups, thus creating a more effective work out.

PDR's bend/arc/range of motion means that as the resistance beam is bent farther away from a plane of minimum resistance, the sustained mechanical resistance incrementally increases, creating a progressively more intense and effective work out/work load on the target muscle group.

Continuous Progressive Dynamic Resistance loading from the bending of VRB's 100 is a highly effective bio-mechanical exercise.

In other aspects of the invention, different types of sport equipment and apparatus may incorporate the VRB 100 technology described herein. Examples in which VRB 100 technology may be applied are:

FlexGym & FlexTrax products represent an apparatus or structure to hold a plurality of rod holders into which VRB 100 resilient adjustable or non-adjustable solid or tubular rods and other exercise apparatus are inserted to allow users to perform a variety of exercises. FIGS. 3, 4 and 5 illustrate an exemplary system in accordance with the principles of the invention.

FlexBoard product represents an apparatus or structure wherein a transportable structural panel resting on the ground with rod holders into which VRB 100 are inserted perpendicularly to allow users to perform a variety of exercises. FIG. 6 illustrates an exemplary FlexBoard system in accordance with the principles of the invention.

FlexGym represents an apparatus or structure wherein the VRB 100 technology of the present invention may be incorporated into a plurality of structural tracks with rod holders providing multiple positions into which the VRB 100 resilient adjustable or non-adjustable solid or tubular rods and other exercise apparatus are inserted to allow users to perform a variety of exercises in an I-formed structure, with a cantilevered bench that folds down or may be a free form bench. In addition, the floor tracks, which also comprise the lower structure of the unit, can be optionally retracted to the vertical tracks when not in use.

In one aspect of the invention, a means to track and record exercise cycles per set of the user may be incorporated. For example, biometric data of the user may be recorded on a smart card, a smart phone, a computer, etc. so exercise cycles can be recorded. In addition, biometric data of the user may be conveyed by magnet, reflector, RFID, Wi-Fi or other means to measure or quantify exercise cycle.

In another aspect of the invention, the exercise apparatus may include sensors (e.g., Wi-Fi) to sense proximity of the user as the user approaches the exercise apparatus. The sensors may also be in communication with a user's smart phone transmitter or other technical means and the exercise apparatus response may be setup to correspond to a user's particular exercise regime.

Another embodiment of the exercise apparatus sensors would recognize a user via sensor or Wi-Fi or iPhone transmitter that would initiate servo-mechanisms to proactively set a customized workout cycle. This would mean that the track holder along the track, be it vertical or horizontal, would be matched to the user's ergonomic body size and requirements.

In another aspect of the invention a video display or monitor may be incorporated to enable a user to receive instructions regarding a particular exercise or to watch one or more programs of interest during the exercise session.

Returning to FIG. 3, FIG. 3 represents a method for incorporating the VRB 100 technology into an apparatus for exercise with one or more anchor points which is represented by the product FlexToner. More specifically, the present invention related to a resilient adjustable or non-adjustable solid or tubular rod exercise apparatus handheld at one or more places and flexed.

Other VRB 100 exercise apparatus applications are, but not limited to, upper and or lower body exercise machines: (e.g. treadmills, stair climbers, elliptical trainers, stationary bikes, mobility, medical, rehabilitative systems that create and control selectable bending strength or resistance ranges with fixed rotation to impart PDR) isolating the upper and or lower body for exercise.

The present invention may be incorporated into devices that provide for low impact/low resistance exercises (e.g., Rehabilitative and Geriatric exercisers) to strengthen and rehabilitate post surgical, bed-ridden, sport injury and or geriatric benefit. Typically, these devices may employ VRBs 100 that are matched to the strength of the user. For example, VRB 100 may be adjusted to provide rigid support during an initial healing phase of a sports injury and then adjusted to provide lesser amount of support to compensate for progress during the healing of the sport injury.

Although, the present invention is described with regard to a plurality of different equipment, it would be recognized that the described equipment are merely examples to which the VRB technology described herein may be applied. The examples provided herein are merely illustrative of the application of the claimed technology and the examples are not intended to limit the subject matter claimed.

In other aspects of the invention, other types of sports equipment and apparatus may incorporate the VRB 100 technology described herein. Examples in which VRB 100 technology may be applied are, but not limited to:

Golf Clubs

Golf clubs may be formed of graphite, wood, titanium, glass fiber or various types of composites or metal alloys. Each varies to some degree with respect to stiffness and flexibility. However, golfers generally carry onto the golf course only a predetermined number of golf clubs.

Varying the stiffness or flexibility of the golf club is not possible, unless the golfer brings another set of clubs of a different construction. Even in that case, however, the selection is still somewhat limited.

Nevertheless, it is impractical to carry a huge number of golf clubs onto the course, each club having a slight nuance of difference in flexibility and stiffness than another. Golf players prefer taking onto the course a set of clubs that are suited to the player's specific swing type, strength and ability.

Returning to FIG. 8, which illustrates an exemplary embodiment of an internal VRB 100 in a hollow shaft (e.g., a golf shaft). As previously discussed, the VRB 100 is centrally raised or lowered within the golf shaft, the fulcrum or kick point is raised or lowered, thereby changing the shaft flex. The 360 degree symmetrical geometry provides a solution for an adjustable golf club and would be fully compliant with the existing USGA rules of golf and assorted international golf associations.

FIG. 13 illustrates an exemplary assembled golf club 1300 comprising a shaft 1305 attached to a club head 1306. Also shown is the club grip 1307 at the top of the shaft. Also illustrated is an internally centrally positioned rod 1310 that can be raised or lowered via a rotatable dial selector helix mechanism 1320 in the grip at the top 1307 of the shaft. Further shown, along the central rod 1310 are O-ring groups 1330*a*, 1330*b*, 1330*c*, 1330*d* precisely positioned at specific shaft kick points to control shaft flex (CPM), as the O-rings make incremental internal shaft wall contact. In this illustrated example, each O-ring group is composed of three O-rings. However, it would be known in the art to increase or decrease (or use a different number of O-rings in each group) without altering the scope of the invention.

Additionally shown is a conical rod tip 1340 with splines 1345 located at the end of the central rod 1310, which incrementally engages a hosel bushing 1350 with corresponding sockets 1345 to form a frictional clutch when compressed into hosel bushing 1350. The engagement of the splines 1345 with the hosel bushing 1350 provides to minimize head rotation for straighter fairway ball strikes.

FIG. 14 illustrates the component parts of the internal mechanism of the club shown in FIG. 13, that provides selectable and incremental flex to customize shaft flexure. Notably a helical or planetary gear selector mechanism 1410 positioned at the top of the grip 1407 with a corresponding helix 1415 at the top of the central rod. In a preferred embodiment, a helix (or screw thread), connected to a central sun gear (see FIG. 22) of the mechanism 1320, raises or lowers the rod to produce shaft flex by raising or lowering the central rod 1310 within the shaft 1305 to make O-Ring groups (1330*a* . . . 1330*d*) contact the shaft walls at precisely located corresponding kick points (See FIG. 15). The conical rod tip 1340 with splines 1345 pushes into the hosel bushing 1350 to create hydrostatic pressure on the internal hosel walls to create an incremental friction clutch or anti head rotating mechanism.

FIG. 15 illustrates exemplary high, medium, low (1510*a*, 1510*b*, 510*c*) and hosel kick point locations (1510*d*) or areas of a hollow modern composite golf shaft 1305. Correspondingly, the central rod O-Ring mechanism (1330*a* . . . 1330*d*) incrementally contacting these zones to attenuate shaft flex by individual O-rings and/or O-ring groups (1330*a* . . . 1330*d*) and bushing internal wall hosel contact, resulting in an incrementally controllable shaft flex.

Figure 16:
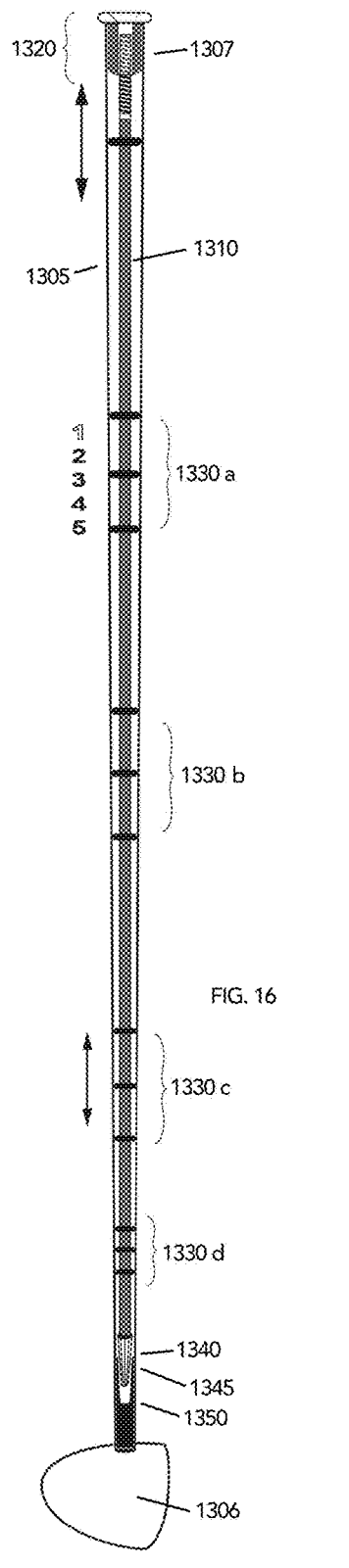
FIG. 16 illustrates an exemplary configuration of the O-ring configuration of the device shown in FIG. 13.

FIG. 16 illustrates an exemplary configuration of the golf club assembly wherein incremental and progressive tangential edges of individual O-rings within corresponding O-ring groups 1330*a* . . . 1330*d* provide outside diameter frictional wall contact within the internal shaft wall of shaft 1305 at corresponding kick points 1610*a* . . . 1610*d*. Specifically, as the internal rod 1310 is raised or lowered within the shaft 1305, the O-ring groups 1330*a* . . . 1330*d* are become incrementally and increasingly in frictional contact with the internal shaft wall of shaft 1305. Thus, the flex in a corresponding kick point 1610*a* . . . 1610*d* is attenuated. Each top to bottom O-ring group 1330*a* . . . 1330*d* has a correspondingly diminishing overall outside diameter matched to the internal slope of the golf shaft 1305 to control the O-ring (and O-ring group) engagement for progressive incremental and progressive frictional wall contact. The outer diameter of each O-ring within a corresponding O-ring group 1310*a* . . . 1310*d* is sized to provide an incremental engagement of the O-ring to contact the inner walls of shaft 1305 as the rod 1310 is raised or lowered to control the level of shaft flexure via attenuation.

Figure 17:
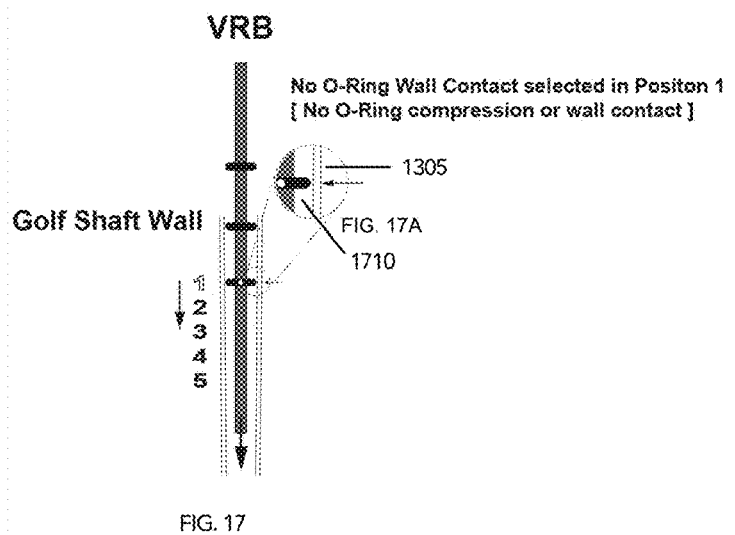
FIG. 17 illustrates a first exemplary configuration of the O-ring configuration of the device shown in FIG. 16 in accordance with the principles of the invention.

FIG. 17 illustrates an exemplary position of an O-ring group 1310*a* positioned such that no contact with the wall of shaft 1305 occurs. Hence, no attenuation of the corresponding kick point exists. As shown, this illustrative position corresponds to a minimum attenuation or maximum flex (i.e., position 1).

FIG. 17A illustrates an expanded view of the exemplary position of an O-ring group shown in FIG. 17. In this illustrated example, a first of the O-rings in the O-ring group (which has the smallest outer diameter of the O-rings within the group) fails to contact the inner wall of shaft 1305. As the remaining O-rings within this O-ring group are positioned above the point of the illustrated first O-ring, these remaining O-rings also fail to contact the inner wall of the conically shape shaft 1305.

Figure 18:
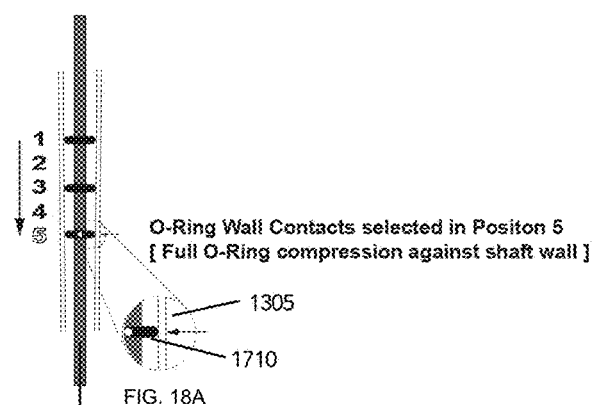
FIG. 18 illustrates a second exemplary configuration of the O-ring configuration of the device shown in FIG. 16 in accordance with the principles of the invention.

FIG. 18 illustrates an exemplary position of an O-ring group 1310*a* positioned such that a maximum contact with the wall of shaft 1305 occurs. Hence, a maximum attention of the corresponding kick point exists. As shown, this illustrative position corresponds to a maximum attenuation or minimum flex (i.e., position 5).

FIG. 18A illustrates an expanded view of the exemplary position of an O-ring group shown in FIG. 18. In this illustrated example, each of the O-rings in the O-ring group contact the conically shape shaft 1305.

Although not shown, it would be recognized that as the central rod is raised from this illustrated position (FIG. 18), the number of O-rings within an O-ring group contacting the inner wall of shaft 1305 decreases causing the degree of attenuation or flex to be altered.

Figure 19:
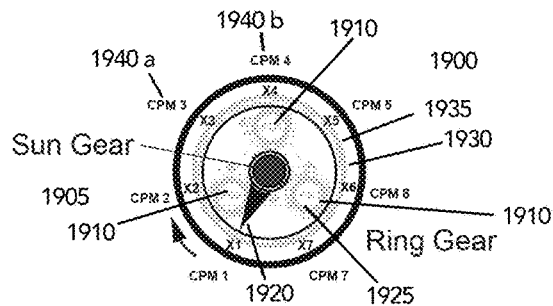
FIG. 19 illustrates a top view of a selection mechanism in accordance with the principles of the invention.

FIG. 19 illustrates an exemplary selector mechanism 1900 suitable for the raising and lowering of central rod 1310 (not shown) within shaft 1305 (not shown). In one aspect of the invention, the selector mechanism, which is represented as a cap 1900 placed on the top of the shaft 1305, includes a planetary gear system comprising a sun gear 1905 positioned at the top of rod 1310 (not shown). Sun gear 1905 includes a plurality of gear teeth (not shown) along its outer circumference. Also shown are a plurality of planetary gears 1910 positioned around the sun gear 1905. Each of the plurality of planetary gears 1910 includes a plurality of gear teeth 1925 along its circumference. The gear teeth (not shown) of the sun gear 1905 engage the gear teeth 1925 of a corresponding one of each of the planetary gear 1910. Three planetary gears 1910 are shown. However, it would be known in the art to increase or decrease the number of planetary gears without altering the scope of the invention. Similarly the number of gear teeth on each of the gear 1905, 1910 may be selected or altered to provide for a desired degree of adjustment of the central rod 1310.

Also shown is a ring gear 1930 positioned along an inner circumference of the cap or selector mechanism 1900. The ring gear 1930 includes a plurality of teeth 1935, which engage the teeth 1925 of a corresponding planetary gear 1910. As the selector mechanism 1900 is turned, the ring gear 1930 turns, due to the engagement of the corresponding gear teeth, the planetary gears 1910, which turn sun gear 1905. Hence, rod 1305 may be raised or lowered based on the direction of the turning of the selection mechanism 1900.

Also shown is an indicia pointer 1920, which illustrates the degree of the lowering or raising of the central rod 1305. Further illustrated are indicia 1940a, 1940b, which provide a visual indication of the level or degree of the lowering or the raising of the central rod 1305.

Figure 20:
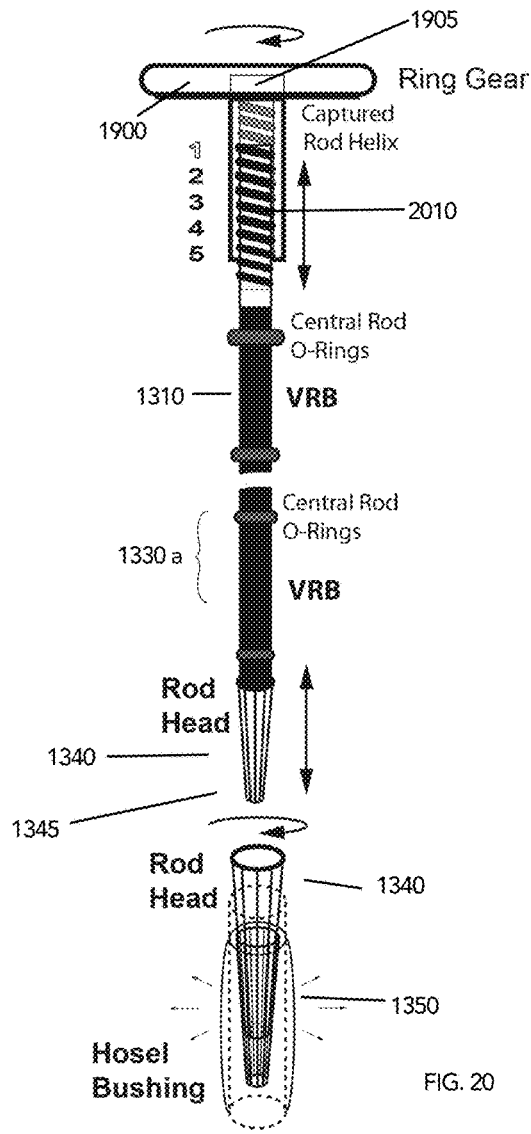
FIG. 20 illustrates an exemplary configuration for rotating the central rod in accordance with the principles of the invention.

FIG. 20 illustrates in further detail the mechanism of the central rod 1310 adjuster using a planetary gear 1900 to rotate or select the vertical position of the central rod 1310 within the shaft 1305 by the preferred ring gear 1930. The outer ring gear situated at the top of the grip is the de-facto shaft flex dial selector that drives the sun gear 1905 that raises or lowers helix 2010 attached to the top of the central rod 1305, which in turn raises or lowers the central rod 1305 incrementally affecting the flex of the shaft 1305. Further illustrated is a more detailed view of the hydrostatic pressure or annular expansion the hosel bushing exhibits when the central rod 1305 is inserted into the hosel bushing 1350. As shown the central rod 1305 includes conical rod tip or head 1340 that may be incrementally inserted into the hosel bushing 1350. Also shown are the splines 1345 that engage the hosel bushing 1350 to prevent slippage of the rod 1305.

Figure 21:
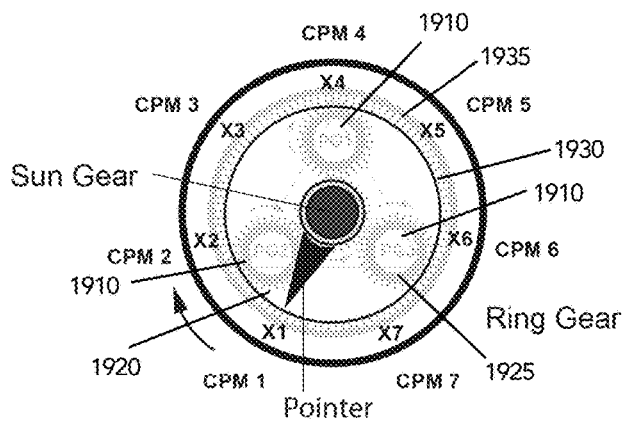
FIG. 21 illustrates a top view of an exemplary planetary gear adjuster in accordance with the principles of the invention.

FIG. 21 illustrates a transparent internal view of the planetary gear selector mechanism 1900 that when rotated, will indicate via indicia the selected flex setting via pointer 1920. Specifically, the planetary gears rotate around the central sun gear (not shown) when the ring gear 1920 is rotated for shaft flex adjustment. As illustrated, the pointer 1920, attached to the sun gear (not shown) points to different indicia (e.g., x1, x2 . . . x7), which correspond to different degrees of flex (CPM 1 . . . CPM 7).

Figure 22:
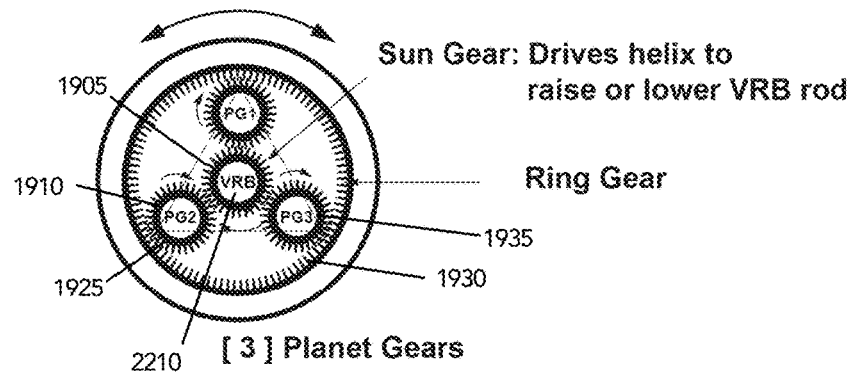
FIG. 22 illustrates a detailed view of the exemplary gear adjuster shown in FIG. 21.

FIG. 22 illustrates an internal cut away view of the planetary gear selector mechanism 1900 with planetary gears 1910 to maximize and balance rotated selection. The outside ring gear 1930 provides the torque to rotate the planetary gears 1910 that provide even smooth adjustment to rotate the central sun gear 1905. As illustrated sun gear 1905 includes gear teeth 2210, which engage the gear teeth 1925 of corresponding 1910. The central rod helix is connected to the sun gear 1905 and is lowered or raised as the Sun gear 1905 rotates.

Figures 23A, 23B, 23C:
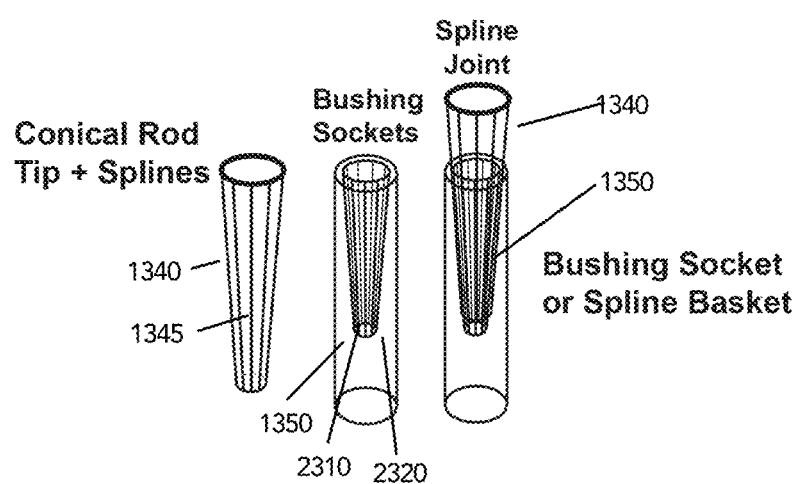
FIGS. 23A-23C illustrate detailed view of the hosel bushing in accordance with the principles of the invention.

FIGS. 23A-23C illustrate views of the central rod cone tip 1340, located at the bottom of the rod 1305, made, in one aspect of the invention, from of polymer for an engineered range of durometer controlled compression, comprising 360° of equally spaced splines 1345, designed to engage a bushing of general similar conical but undersized shape, with corresponding 360° sockets to lock with the splines 1345 when fully engaged or compressed from the central rod 1305 at each incremental flex or compression setting. When the cone tip 1340 engages the bushing 1350 a friction clutch or spline joint is created, along with incremental hydrostatic pressure, providing anti-head rotation mechanism.

FIG. 23A illustrates the central rod tip 1340 including a plurality of splines 1345. FIG. 23B illustrates the conically shaped hollow, container or holder 2310 within the hosel bushing 1350 and matching splines 2320. The conically shaped hollow may include a flexible material (not shown) that allows the tip element 1340 to compress the material to provide a compression force between the tip 1340 and the hollow 2310. FIG. 23C illustrates an exemplary engagement of the central rod tip 1340 into the container or holder 2310 within the hosel bushing.

Figures 24A, 24B, 24C:
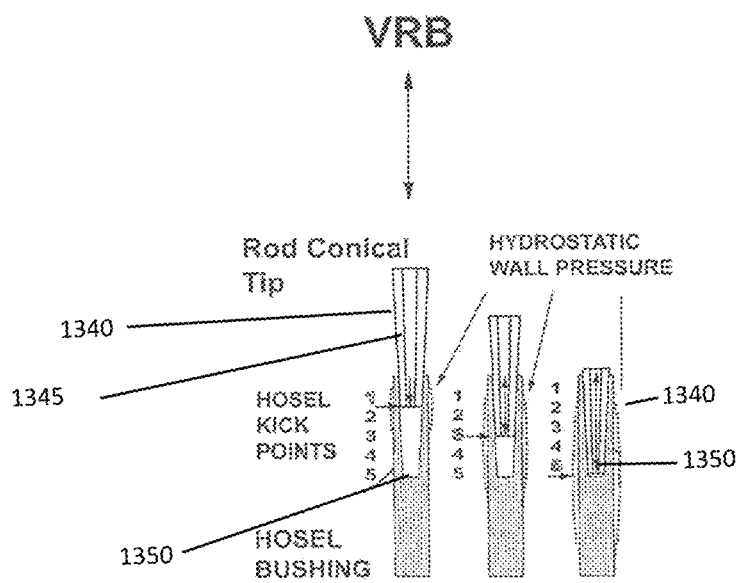
FIGS. 24A-24C illustrate a cross-sectional view of the connection between the central rod and the hosel bushing in accordance with the principles of the invention.

FIGS. 24A-24C illustrate side views of the rod conical tip 1340 progressively or incrementally engaging the holder 2310 within hosel bushing 1350 and due to the slightly oversized tip, creating incremental radial volume displacement or hydrostatic pressure against the neck of interior hosel holder 2210 wall progressively for each increased flex setting. The radial pressure applied by the tip to the internal walls of the holder 2310 holds the hosel and acts as an incremental anti-head rotation mechanism.

Although the invention claimed as been described with regard to a rotary selection mechanism (e.g., a planetary gear) it would be recognized that the selection mechanism may further comprise another rotary mechanism such as the illustrated worm gear or spline/socket or may comprise a linear mechanism such as a push or pull, which allows for incremental changes in the raising or lowering of the central rod. For example, the shaft may include a plurality of holes positioned vertically along the shaft. The central rod may include a protrusion which engages one of the vertically positioned holes. The engagement of the protrusions within one of the vertically positioned holes determines the position of the central rod within the shaft (and consequently, the flex).

Running Shoes, Training Shoes, Basketball Shoes

The transmission of the shoe wearer's strength (power) from their legs into the ground is directly affected by the sole stiffness of the shoe. Runners may gain more leverage and, thus more speed, by using a stiffer sole. Basketball players may also affect the height of their jumps through the leverage transmitted by the sole of their shoes. If the sole is too stiff, however, the toe-heel flex of the foot is hindered.

It is advantageous that the shoe wearer have the ability to tailor the sole stiffness to his/her individual weight, strength, height, running style, and ground conditions. Preferably, the shoe wearer may tailor the stiffness of the shoe sole to affect the degree of power and leverage that is to be transmitted from the wearer into the ground.

In this example, VRB 100 is insertable, insert molded or structurally connected to the shoe sole in lateral and/or longitudinal positions within the sole and are all rotatable to a fixed and mechanically locked position to effect custom flexural resistance range. Additionally, zones of resistance are customizable, e.g. the right pad of the foot can be made more rigid than the left pad side through the beam's rotated orientation. Thus, the degree of flexibility may be customized to accommodate a user's desired preferences.

Incorporation of the VRB 100 technology into running shoes, as shown in FIG. 11, provides a dynamic adjustable in-sole suspension system that can absorb the weight of the wearer and release it per each step.

Hockey Sticks

Hockey includes, but is not limited to, ice hockey, street hockey, roller hockey, field hockey and floor hockey.

Hockey players may require that the flexure of the hockey stick be changed to better assist in the wrist shot or slap shot needed at that particular junction of a game or which the player was better at making. Players may not usually leave the field to switch to a different piece of equipment during play.

Younger players may require more flex in the hockey stick due to lack of strength and such flex may mean the difference between the younger player being able to lift the puck or not when making a shot since a stiffer flex in the stick may not allow the player to achieve such lift.

In addition, as the younger players ages and increases in strength, the player may desire a stiffer hockey stick, which in accordance with convention means the hockey player would need to purchase additional hockey stick shafts with the desired stiffness and flexibility characteristics. Indeed, to cover a full range of nuances of differing stiffness and flexibility characteristics, hockey players would have available many different types of hockey sticks.

Even so, the hockey player may merely want to make a slight adjustment to the stiffness or flexibility of a given hockey stick to improve the nuances of the play. Thus, the incorporation of the VRB technology into hockey sticks (shaft and/or blade) provides for variations in the stiffness and flexibility that may be adjusted as the user progresses in their ability.

Incorporation of the VRB technology into hockey sticks is similar to that shown in FIG. 7.

In other aspects of the invention, different type of Do-it-Yourself (DIY) and Home Improvement products and devices may incorporate the VRB technology described herein. Examples in which VRB technology may be applied are:

Lawn Equipment:

Adjustable lawn rake with VRB 100 tines:

The VRB 100 technology described by the present invention may be incorporated into a lawn rake. In this case, an adjustable rake with a rotatable VRB 100 down the shaft of the rake may be created. The VRB 100 facilitates the adjustment of the lawn rake, with the ability to adjust stiffness of the shaft relative to the load (e.g., light grass clippings, heavy grass clipping, wet grass clippings).

Incorporation of the VRB 100 technology into lawn rake (or other similar handled devices) is similar to that shown in FIGS. 10A and 10B.

In another embodiment, the VRB 100 technology described by the present invention may be incorporated into tines of a lawn rake creating an adjustable rake. Thus, the VRB 100 facilitates the adjustment of a lawn/utility rake by providing the ability to create variable shaft resistance for light or heavy duty gravel raking due to its rotated orientation. The VRB 100 adjustment setting may simultaneously rotate the rake's tines from 0° to 90°, thus affecting a stiffer tine orientation. The tines may be elliptical or oval in shape in an embodiment of an elliptical VRB 100. When the tines are in a 0° orientation, they are the most flexible and suitable for raking leaves or light duty yard work. When the tines are in a 90° orientation, they are the most rigid and suitable for raking heavy duty gravel. The flexural change of tines can be further impacted by means of adjusting where the center point of a fulcrum of the flex of tines is located.

FIG. 10A illustrates an exemplary lawn rake incorporating the VRB 100 technology disclosed herein. FIGS. 10A and 10B illustrate a rake assembly 1000 including a handle 1010 and a tine assembly 1015 including a plurality of VRB 100 tines that are simultaneously adjusted through rotation. FIG. 10B illustrates a bottom view of rake 1000 showing the orientation of the tines 100 at a maximum resistance level (90 degree orientation).

Thus, the incorporation of the VRB 100 technology in the tines creates a flexible lawn rake to alter the flex characteristics of the rake.

Although, the present invention is described with regard to a plurality of different lawn equipment, it would be recognized that the lawn equipment described herein are merely examples to which the VRB technology described herein may be applied. The examples provided herein are merely illustrative of the application of the claimed technology and the examples are not intended to limit the subject matter claimed.

In other aspects of the invention, different type of medical products and devices may incorporate the VRB technology described herein. Additional examples in which VRB technology may be applied are: Mobility assistance and Rehabilitative Braces that provide dynamic support and suspension for joints and orthotic braces: Foot, ankle, knee, hip, back, shoulder, elbow, wrist, neck (i.e., Prophylactic, Functional Support, Post-operative, Unloader and or Extreme Sports, acting as a second compression driven reactive joint, et al.).

In this aspect of the invention, the VRB 100 may be used to create a medical brace or orthotic device that by provides a dynamic support and suspension system with variable and adjustable resistance settings to achieve an adjustable performance range so as to customize the brace or device during the recuperation stage of the wearer, acting as external supporting spring ligament or adjustable box spring structure and/or further supported by a conformal brace framework. For example the conformal brace framework may be a mechanical joint and/or a flexible webbing, e.g., Ballistic nylon/Neoprene et al.

In one aspect of the invention, the medical brace or orthotic device may be used to:

1. control, guide, limit and/or immobilize an extremity, joint or body segment for a particular reason;
2. To restrict movement in a given direction;
3. To assist movement generally;
4. To reduce weight bearing forces for a particular purpose;
5. To aid rehabilitation from fractures after the removal of a cast; and
6. To otherwise correct the shape and/or function of the body, to provide easier movement capability or reduce pain.

Although, the present invention is described with regard to knee brace, FIG. 12, it would be recognized that the described braces are merely examples to which the VRB technology described herein may be applied. The examples provided herein are merely illustrative of the application of the claimed technology and the examples are not intended to limit the subject matter claimed. For example, the VRB technology described herein may be applied to braces that are used for the back, arm, elbow, neck, and legs, without altering the scope of the invention.

In another aspect of the VRB technology described herein, braces or devices may be constructed wherein the VRB beams are equipped with attached sensors [e.g. Electrogoniometer] to provide continuous bio-mechanic feedback or other biomechanical sensor means of medical or injury diagnostic. For example, compression, extension, articulation, range and/or twisting measurements may be made and provided to a network (e.g., a WI-FI, wireless) to monitor the movement of the user.

In another aspect of the invention, the braces, including the VRB technology described herein, may include sensors, such as impedance wire sensors, accelerometer, stressors, etc., to measure flexural strength, cycle counts per day to measure Joint performance, injury, damage assessment, etc., so that an appropriate monitoring of the healing of the effected joint may be monitored. Such monitoring is valuable in the field of professional sports medicine, for example.

In still another embodiment of the VRB technology described herein provides further benefits in the medical profession, wherein a VRB may be made from a bio-degradable polymer that may be incorporated into an Internal Fixation brace. In this case, the internal VRB may be rotatable using outside setting pins connected to an internal worm gear at the head of the internal VRB. The main benefit of bio-degradable VRB fixation beams is that they require no post-operative surgery to remove. The biopolymers may be of a non-toxic material capable of maintaining strong mechanical integrity until engineered to degrade, wherein controlled rates of degradation (typically a function of crystallinity) are predetermined. An additional benefit is to not create an immune response and or the products of degradation must also be non-toxic.

Controlled degradation rates may be affected by a percentage of polymer crystallinity, molecular weight, hydrophobicity and location within the body.

Examples of promising biodegradable polymers to be made into VRBs through extrusion and or injection molding are, but not limited to, 3-hydroxypropionic acid, the suture polymer Polyglycolide and or Poly(lactic acid) or polylactide (PLA). A thermoplastic aliphatic polyester that degrades into lactic acid, a natural waste product of the body.

Although the different applications of the VRB shown herein refer to VRB 100 (type I), it would be recognized that each of the applications may incorporate one or more of the other type of VRBs (i.e., type II through type VII) without altering the scope of the invention.

The specification is to be regarded in an illustrative manner, rather than with a restrictive view, and all such modifications are intended to be included within the scope of the invention.

Benefits, advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated. For example, any numerical values presented herein are considered only exemplary and are presented to provide examples of the subject matter claimed as the invention. Hence, the invention, as recited in the appended claims, is not limited by the numerical examples provided herein.

What is claimed:

1. An adjustment mechanism for controlling the flex of a golf club comprising:
    a hollow shaft,
    a cap on a first end of the hollow shaft; and
    a club head attached to a second end of the hollow shaft by a hosel bushing;
    the adjustment mechanism comprising:
        a hollow cylindrical central rod positionable within said hollow shaft, wherein the central rod is positionably insertable within the hosel bushing;
        at least one group of rings circumferentially positioned about the central rod, each of the at least one group of rings including at least one ring, each of the at least one ring sized to contact an inner wall of the hollow shaft at designated regions along the inner wall; and
        a selection mechanism, comprising a planetary gear system, incorporated into the cap, engaging a top of the central rod, said selection mechanism configured to:
            alter a position of said central rod within said hollow shaft.

2. The adjustment mechanism of claim 1, wherein the central rod within the hollow shaft is at least one of: rotational positionable and linearly positionable.

3. The adjustment mechanism of claim 1, further comprising:
    a flexible material in communication with said central rod at a lower end of said rod, wherein said position of said central rod is lowered within the hollow shaft by compressing the flexible material.

4. The adjustment mechanism of claim 1, wherein said central rod comprises:
    a center portion having a cylindrical shape.

5. The adjustment mechanism of claim 4, wherein said central rod further comprises:
    a conically shaped tip portion engaging the hosel bushing.

6. The adjustment mechanism of claim 5, wherein the hosel bushing comprises:
    a conically shaped hollow sized smaller than the conically shaped tip portion.

7. The adjustment mechanism of claim 6 wherein the conically shaped tip portion comprises at least one spline.

8. The adjustment mechanism of claim 4, wherein said tip portion comprises:
    at least one spine.

9. The adjustment mechanism of claim 1, wherein the adjustment mechanism is incorporated in-line with the rod.

10. The adjustment mechanism of claim 1, further comprising:
    a plurality of graduated indicia incorporated into said cap.

11. A golf club comprising:
    a hollow shaft comprising a first end, comprising: a first end, attached to a golf head by a hosel, and a second end;
    a hollow rod, having a circular cross-section, positioned internally to, and along a longitudinal axis of, the hollow shaft, said hollow rod selectably insertable into the hosel;
    a cap fixed on the second end, the cap comprising:
        an adjuster, comprising a planetary gear system, configured to:
            perform one of: raise the hollow rod within the hollow shaft and lower the hollow rod within the hollow shaft; and
        a plurality of indicia indicating a position of the rod within the hollow shaft.

12. The golf club of claim 11, wherein the cap is rotatable about said second end.

13. The golf club of claim 11, wherein the hollow rod comprises:
    a substantially cylindrical rod section; and
    a conically shaped tip section, said tip section comprising at least one spline, said tip section configured to engage the hosel.

14. The golf club of claim 13, wherein the hosel comprises:
    a conical shaped hollow, said conically shaped hollow sized smaller than the tip section.

15. The golf club of claim 11, further comprising:
    at least one group of rings position circumferentially about the hollow rod, each of the at least one group of rings including at least one ring.

16. The golf club of claim 15, wherein each of the at least one ring is sized to selectively engage at least one position along an inner wall of the hollow shaft.

17. The golf club of claim 11, wherein the adjuster is configured to:

engage a helix on the rod.

\* \* \* \* \*